(12) United States Patent
Yl et al.

(10) Patent No.: US 11,540,785 B2
(45) Date of Patent: Jan. 3, 2023

(54) X-RAY IMAGE PROCESSING METHOD AND X-RAY IMAGE PROCESSING APPARATUS

(71) Applicant: SAMSUNG ELECTRONICS CO., LTD., Suwon-si (KR)

(72) Inventors: Jaemock Yl, Suwon-si (KR); Chaeyeong Lee, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 358 days.

(21) Appl. No.: 16/751,319

(22) Filed: Jan. 24, 2020

(65) Prior Publication Data

US 2020/0237319 A1    Jul. 30, 2020

(30) Foreign Application Priority Data

Jan. 25, 2019    (KR) .................. 10-2019-0010064

(51) Int. Cl.
*A61B 6/00*    (2006.01)
*A61B 6/02*    (2006.01)
(Continued)

(52) U.S. Cl.
CPC ............ *A61B 6/022* (2013.01); *A61B 6/5205* (2013.01); *G06T 7/0012* (2013.01);
(Continued)

(58) Field of Classification Search
CPC ..... A61B 6/022; A61B 6/5205; A61B 6/5282; A61B 6/505; A61B 6/5235; A61B 6/461; A61B 6/5217; G06T 7/0012; G06T 11/005; G06T 2207/10116; G06T 2207/30008; G06T 11/003

See application file for complete search history.

(56) References Cited

U.S. PATENT DOCUMENTS 6,683,934 B1    1/2004    Zhao et al.
7,068,826 B2    6/2006    Jabri et al.
(Continued)

FOREIGN PATENT DOCUMENTS

EP    3 351 176 A1    7/2018
JP    5389965 B2    1/2014
(Continued)

OTHER PUBLICATIONS

Communication dated Jun. 9, 2020, from the European Patent Office in European Application No. 20153699.2.
(Continued)

*Primary Examiner* — Courtney D Thomas
(74) *Attorney, Agent, or Firm* — Sughrue Mion, PLLC

(57) ABSTRACT

An X-ray image processing method, including obtaining a first X-ray image of an object including a plurality of materials including a first material and a second material; obtaining a first partial image generated by imaging the first material and a second partial image generated by imaging the first material overlapping the second material from the first X-ray image; obtaining first information related to a stereoscopic structure of the first material, based on the first partial image included in the first X-ray image; and obtaining second information about the second material based on the first information and the second partial image.

20 Claims, 14 Drawing Sheets

(51) Int. Cl.
    *G06T 7/00*         (2017.01)
    *G06T 11/00*       (2006.01)

(52) U.S. Cl.
    CPC ... *G06T 11/005* (2013.01); *G06T 2207/10116* (2013.01); *G06T 2207/30008* (2013.01)

(56) References Cited

U.S. PATENT DOCUMENTS

| | | |
|---|---|---|
| 7,856,133 B2 | 12/2010 | Nukui |
| 9,907,528 B2 | 3/2018 | Yi et al. |
| 2003/0194120 A1 | 10/2003 | Unger et al. |
| 2003/0215120 A1 | 11/2003 | Uppaluri et al. |
| 2006/0008046 A1 | 1/2006 | Ruhrnschopf |
| 2012/0170826 A1* | 7/2012 | Jang .................. A61B 6/4007 |
| | | 382/132 |
| 2013/0148776 A1 | 6/2013 | Lee et al. |
| 2016/0213344 A1 | 7/2016 | Yi et al. |

FOREIGN PATENT DOCUMENTS

| | | |
|---|---|---|
| JP | 5640280 B2 | 12/2014 |
| KR | 10-2009-0079867 A | 7/2009 |

OTHER PUBLICATIONS

Communication dated Jun. 30, 2020, from the European Patent Office in European Application No. 20153662.0.

\* cited by examiner

X-RAY IMAGE PROCESSING METHOD AND X-RAY IMAGE PROCESSING APPARATUS

CROSS-REFERENCE TO RELATED APPLICATION

This application is based on and claims priority under 35 U.S.C. § 119 to Korean Patent Application No. 10-2019-0010064, filed on Jan. 25, 2019, in the Korean Intellectual Property Office, the disclosure of which is incorporated by reference herein in its entirety.

BACKGROUND

1. Field

The disclosure relates to an X-ray image processing method for obtaining information related to an object by analyzing an X-ray image of the object and an X-ray image processing apparatus using the X-ray image processing method.

2. Description of Related Art

An X-ray apparatus may be a medical imaging apparatus that obtains images of internal structures of an object by transmitting an X-ray through the human body. The X-ray apparatus may obtain medical images of an object more simply and within a shorter time than other medical imaging apparatuses including a magnetic resonance imaging (MRI) apparatus and a computed tomography (CT) apparatus. Therefore, the X-ray apparatus may be widely used for simple chest imaging, simple abdomen imaging, simple skeleton imaging, simple nasal sinuses imaging, simple neck soft tissue imaging, and breast imaging.

X-rays are electromagnetic waves having wavelengths ranging from 0.01 Å to 100 Å, and may be transmitted through an object and thus are widely used in medical devices for imaging the inside of a living body or are used in non-destructive testing devices in industrial areas.

An X-ray apparatus using X-rays may obtain an X-ray image of an object by transmitting X-rays emitted from an X-ray source through the object and detecting a strength difference between the transmitted X-rays by using an X-ray detector. Accordingly, an internal structure of the object may be detected and the object may be diagnosed by using the X-ray image. The X-ray apparatus easily detects the inner structure of the object by using the fact that transmittances of the X-rays vary according to a density of the object and atomic numbers of atoms included in the object. As a wavelength of an X-ray decreases, a transmittance increases and a brightness of a screen increases.

An X-ray apparatus may generate a front image of an object by two-dimensionally imaging the object. Accordingly, one X-ray image obtained through one X-ray imaging operation may not be suitable for measuring a stereoscopic structure of the object, a measurement value (e.g., a thickness of an organ or tissue in the object) corresponding to the stereoscopic structure of the object, or characteristic values (e.g., a volume of fat in the object) of a plurality of different materials of the object.

Recently, apparatuses and methods have been developed for obtaining a stereoscopic structure of an object, a measurement value (e.g., a thickness of an organ or tissue in the object) corresponding to the stereoscopic structure of the object, or characteristics values (e.g., a volume of fat in the object) of a plurality of different materials of the object by using a plurality of X-ray images obtained through multiple X-ray imaging operations that emit X-rays having a plurality of energy bands to the object.

However, because X-rays emitted to an object for X-ray imaging are radioactive, the X-rays are harmful to humans. Accordingly, a user may desire to perform X-ray imaging while minimizing a radiation dose exposed to a patient including an object to be imaged. Accordingly, when X-ray imaging is performed multiple times as described above, a radiation dose exposed to the patient is increased.

Also, an accurate diagnosis may more easily be made when information about materials of an object is more accurately measured from an X-ray image. Hence, it is necessary to more rapidly and accurately measure the information about the materials of the object from the X-ray image.

Accordingly, there is a demand for a method and apparatus for accurately obtaining various information about an object while minimizing a radiation dose exposed to a patient or the number of times X-ray imaging is performed.

SUMMARY

Provided are an X-ray image processing method of obtaining information about two or more different materials included in an object by using one X-ray image and an X-ray image processing apparatus using the X-ray image processing method.

Particularly provided are an X-ray image processing method of obtaining information about soft tissue and bones by using a first X-ray image obtained by emitting an X-ray having a single energy band to an object and an X-ray image processing apparatus using the X-ray image processing method.

Additional aspects will be set forth in part in the description which follows and, in part, will be apparent from the description, or may be learned by practice of the presented embodiments of the disclosure.

In accordance with an aspect of the disclosure, an X-ray image processing method includes obtaining a first X-ray image of an object including a plurality of materials including a first material and a second material; obtaining a first partial image generated by imaging the first material and a second partial image generated by imaging the first material overlapping the second material from the first X-ray image; obtaining first information related to a stereoscopic structure of the first material, based on the first partial image included in the first X-ray image; and obtaining second information about the second material based on the first information and the second partial image.

The first material may be soft tissue, and the second material may be a bone.

The first information may include information about a thickness of the soft tissue included in the first partial image.

The second information may include information about a thickness of the bone included in the second partial image, and the second information may be obtained based on the information about the thickness of the soft tissue and the second partial image.

The second partial image may be adjacent to the first partial image in the first X-ray image, and the second partial image may include a region corresponding to a boundary between the bone and the soft tissue.

The X-ray image processing method may further include outputting a user interface screen including at least one of the first information and the second information.

The X-ray image processing method may further include obtaining third information corresponding to a stereoscopic distribution of at least one of the soft tissue or the bone, based on the first information and the second information.

The X-ray image processing method may further include performing scatter correction on the first X-ray image based on the first information and the second information, and updating the first information and the second information based on the scatter-corrected first X-ray image.

The X-ray image processing method may further include generating a scatter map corresponding to a scattered X-ray component in the first X-ray image, based on the first information and the second information.

The X-ray image processing method may further include removing a noise component corresponding to a scattered X-ray in the first X-ray image, based on the scatter map.

The X-ray image processing method may further include obtaining a first virtual X-ray image indicating the object, wherein the first virtual X-ray image is generated through projection simulation based on the first information, the second information, and the scatter map; and determining whether to update the scatter map, based on a result of a comparison between the first virtual X-ray image and the first X-ray image.

The first X-ray image may be obtained by emitting an X-ray having a single energy band to the object.

In accordance with an aspect of the disclosure, an X-ray image processing apparatus includes: a data interface configured to obtain a first X-ray image of an object including a plurality of materials including a first material and a second material; and a controller including at least one processor configured to execute at least one instruction to: obtain a first partial image generated by imaging the first material and a second partial image generated by imaging the first material overlapping the second material from the first X-ray image, obtain first information related to a stereoscopic structure of the first material based on the first partial image included in the first X-ray image, and obtain second information about the second material based on the first information and the second partial image.

The first material may be soft tissue, and the second material may be a bone.

The first information may include information about a thickness of the soft tissue included in the first partial image, the second information may include information about a thickness of the bone imaged in the second partial image, and the second information may be obtained based on the information about the thickness of the soft tissue and the second partial image.

The second partial image may be adjacent to the first partial image in the first X-ray image, and the second partial image may include a region corresponding to a boundary between the bone and the soft tissue.

The at least one processor may be further configured to: perform scatter correction on the first X-ray image based on the first information and the second information, and update the first information and the second information based on the scatter-corrected first X-ray image.

The at least one processor may be further configured to generate a scatter map corresponding to a scattered X-ray component in the first X-ray image, based on the first information and the second information.

The at least one processor may be further configured to execute the at least one instruction to obtain a first virtual X-ray image indicating the object, wherein the first virtual X-ray image is generated through projection simulation based on the first information, the second information, and the scatter map, and determine whether to update the scatter map, based on a result of a comparison between the first virtual X-ray image and the first X-ray image.

In accordance with an aspect of the disclosure, a non-transitory computer-readable medium stores instructions which, when executed by at least one processor, cause the at least one processor to perform an X-ray image processing method, the X-ray image processing method including obtaining a first X-ray image of an object including a plurality of materials including a first material and a second material; obtaining a first partial image generated by imaging the first material and a second partial image generated by imaging the first material overlapping the second material from the first X-ray image; obtaining first information related to a stereoscopic structure of the first material, based on the first partial image included in the first X-ray image; and obtaining second information about the second material based on the first information and the second partial image.

BRIEF DESCRIPTION OF THE DRAWINGS

The above and other aspects, features, and advantages of certain embodiments will be more apparent from the following description taken in conjunction with the accompanying drawings, in which.

DETAILED DESCRIPTION

Figure 1:
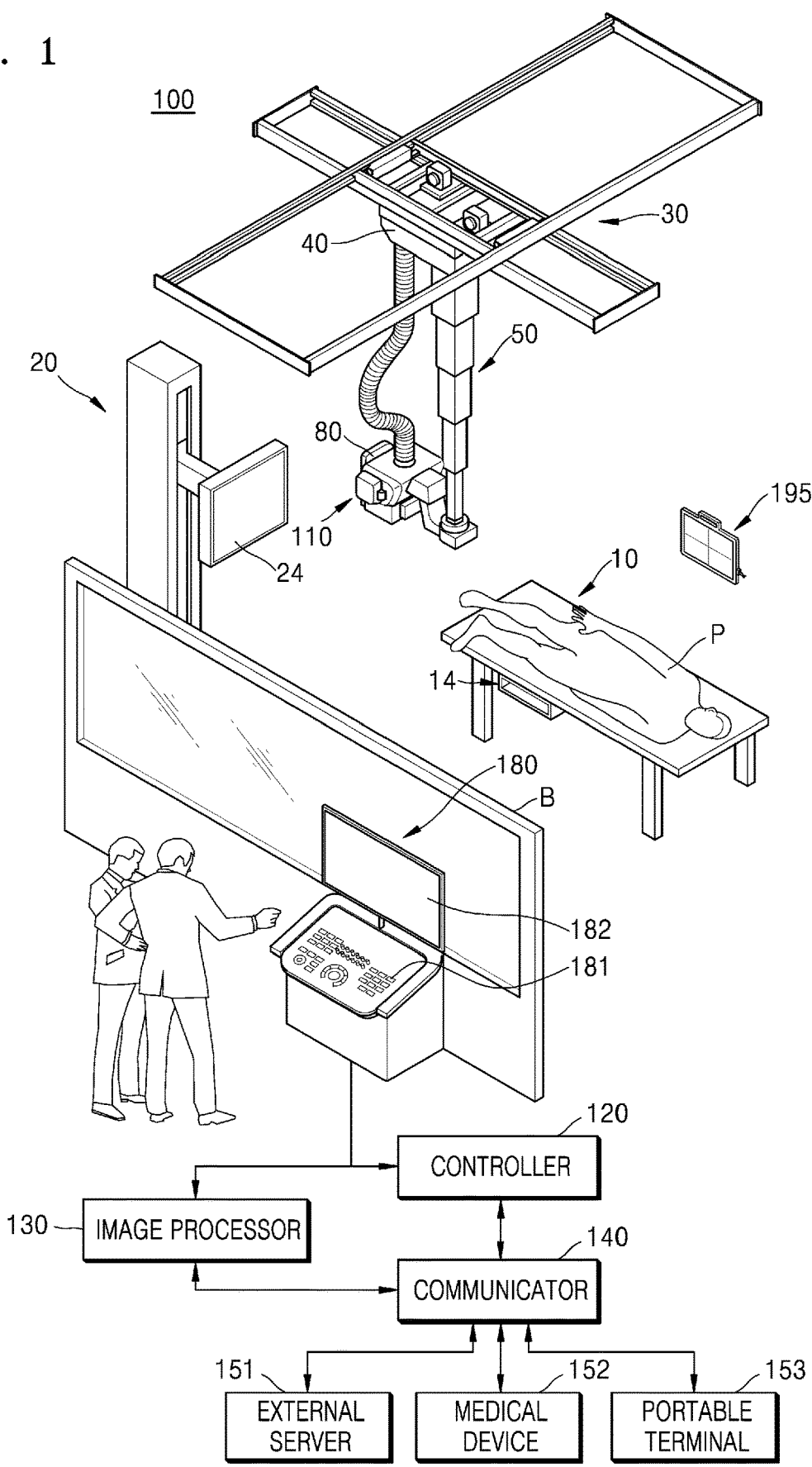
FIG. 1 is a view illustrating a configuration of an X-ray apparatus.

Hereinafter, principles and embodiments of the disclosure will be described in detail in order to fully convey the scope of the disclosure and enable one of ordinary skill in the art to embody and practice the disclosure. The embodiments may be implemented in various forms.

The same reference numerals denote the same elements throughout the specification. All elements of embodiments are not described in the specification, and descriptions of matters well known in the art to which the disclosure pertains or repeated descriptions between embodiments will be omitted. Terms such as "part" and "portion" used herein denote those that may be embodied by software or hardware. According to embodiments, a plurality of parts or portions may be embodied by a single unit or element, or a single part or portion may include a plurality of elements. Operation principles and embodiments will now be explained with reference to the accompanying drawings.

Throughout the disclosure, the expression "at least one of a, b or c" indicates only a, only b, only c, both a and b, both a and c, both b and c, all of a, b, and c, or variations thereof.

An image used herein may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object," which is a thing to be imaged, may include a human, an animal, or a part thereof. For example, an object may include a body part (e.g., an organ) or a phantom.

FIG. 1 is a view illustrating a configuration of an X-ray apparatus according to an embodiment. FIG. 1 will be described assuming that the X-ray apparatus is a fixed X-ray apparatus.

Referring to FIG. 1, an X-ray apparatus 100 includes an X-ray emitter 110 that generates and emits an X-ray, an X-ray detector 195 that detects the X-ray emitted from the X-ray emitter 110 and transmitted through an object, and a workstation 180 that receives a command from a user and provides information. Also, the X-ray apparatus 100 may include a controller 120 that controls the X-ray apparatus 100 according to the input command and a communicator 140 that communicates with an external device.

Some or all of elements of the controller 120 and the communicator 140 may be included in the workstation 180 or may be provided separately from the workstation 180.

The X-ray emitter 110 may include an X-ray source that generates an X-ray and a collimator that adjusts an emission region of the X-ray generated by the X-ray source.

A guide rail 30 may be provided on the ceiling of an examination room in which the X-ray apparatus 100 is located, the X-ray emitter 110 may be connected to a movable carriage 40 that moves along the guide rail 30 to move the X-ray emitter 110 to a position corresponding to an object P, and the movable carriage 40 and the X-ray emitter 110 may be connected through a foldable post frame 50 to adjust a height of the X-ray emitter 110.

An input interface 181 that receives a command of the user and a display 182 that displays information may be provided in the workstation 180.

The input interface 181 may receive a command for an imaging protocol, imaging conditions, imaging timing, and position control of the X-ray emitter 110. Examples of the input interface 181 may include a keyboard, a mouse, a touchscreen, a voice recognizer, etc.

The display 182 may display a screen for guiding the user's input, an X-ray image, a screen showing a state of the X-ray apparatus 100, etc.

The controller 120 may control imaging timing, imaging conditions, etc. of the X-ray emitter 110 according to a command input from the user, and may generate a medical image by using image data received from the X-ray detector 195. Also, the controller 120 may control a position or a posture of a mounting portion 14 or 24 on which the X-ray emitter 110 or the X-ray detector 195 is mounted according to a position of the object P and an imaging protocol.

The controller 120 may include a memory in which a program for performing the above operations and following operations is stored and a processor for executing the stored program. The controller 120 may include a single processor or may include a plurality of processors, and in the latter case, the plurality of processors may be integrated on one chip or may be physically separated.

The X-ray apparatus 100 may be connected to an external device 150 (e.g., an external server 151, a medical device 152, or a portable terminal 153 (e.g., a smartphone, a tablet PC, or a wearable device)) through the communicator 140 and may transmit or receive data to or from the external device 150.

The communicator 140 may include one or more elements that enable communication with the external device 150, and may include at least one of, for example, a short-range communication module, a wired communication module, or a wireless communication module.

Also, the communicator 140 may receive a control signal from the external device 150, may transmit the received control signal to the controller 120, and may cause the controller 120 to control the X-ray apparatus 100 according to the received control signal.

Also, the controller 120 may control the external device 150 according to a control signal of the controller 120 by transmitting the control signal to the external device 150 through the communicator 140. For example, the external device 150 may process data of the external device 150 according to the control signal of the controller 120 received through the communicator 140.

Also, the communicator 140 may further include an internal communication module that enables communication among elements of the X-ray apparatus 100. A program for controlling the X-ray apparatus 100 may be installed in the external device 150, and may include instructions for performing some or all of operations of the controller 120.

The program may be previously installed in the portable terminal 153, or a user of the portable terminal 153 may download the program from a server that provides an application and may install the program. A recording medium in which the program is stored may be included in the server that provides the application.

The X-ray detector 195 may be implemented as a fixed X-ray detector fixed to a stand 20 or a table 10, may be detachably mounted on the mounting portion 14 or 24, or may be implemented as a portable X-ray detector that may be used at any position. The portable X-ray detector may be implemented as a wired detector or a wireless detector according to a data transmission method and a power supply method.

The X-ray detector 195 may be included or may not be included in the X-ray apparatus 100. In the latter case, the X-ray detector 195 may be registered in the X-ray apparatus 100 by the user. Also, in both cases, the X-ray detector 195 may be connected to the controller 120 through the communicator 140 and may receive a control signal or may transmit image data.

A sub-user interface 80 that provides information to the user and receives a command from the user may be provided on a side surface of the X-ray emitter 110 and may perform some or all of functions of the input interface 181 and the display 182 of the workstation 180.

When all or some of elements of the controller 120 and the communicator 140 are provided separately from the workstation 180, the elements may be included in the sub-user interface 80 provided on the X-ray emitter 110.

Although the X-ray apparatus 100 is a fixed X-ray apparatus connected to the ceiling of the examination room in FIG. 1, the X-ray apparatus 100 may include an X-ray apparatus having any of various structures known to one of ordinary skill in the art such as a C-arm X-ray apparatus or a mobile X-ray apparatus.

An X-ray image (specifically, a first X-ray image) according to an embodiment may be obtained by the X-ray apparatus 100 of FIG. 1. In detail, the X-ray apparatus 100 may obtain an X-ray image of an object through X-ray imaging or raw data used to obtain the X-ray image. For example, when the X-ray detector 195 detects an X-ray transmitted through the object, the raw data may be a signal obtained by electrically converting the number of X-ray photons detected by the X-ray detector 195.

In order to easily read an X-ray image or easily make a diagnosis by using the X-ray image, an X-ray image processing apparatus may analyze the X-ray image obtained through X-ray imaging and may use an analysis result. The X-ray image that is obtained by emitting an X-ray to an object of a patient and detecting the X-ray passing through the object may be a medical image showing the inside of the object. Also, the X-ray image may refer to not only an image visually representing the object but also data obtained to generate the image.

Hereinafter, a medical image obtained by directly emitting an X-ray to the object of the patient and performing X-ray imaging by using the X-ray apparatus 100 is referred to as an 'X-ray image', and an X-ray image obtained without directly emitting an X-ray to the object of the patient through X-ray imaging is referred to as a 'virtual X-ray image'.

In an embodiment, the X-ray image processing apparatus may refer to an electronic device that may i) obtain predetermined information by using an X-ray image, ii) may obtain diagnostic information by analyzing the X-ray image, or iii) may process, generate, correct, update, or display all images or information used for diagnosis based on the X-ray image.

In detail, the X-ray image processing apparatus according to an embodiment may be an electronic device that decomposes a plurality of different materials (e.g., bones and soft tissue) and obtains information about each of the plurality of different materials based on an X-ray image.

Also, the X-ray image processing apparatus according to an embodiment may analyze an X-ray image obtained by the X-ray apparatus 100 in a computer and may generate and/or use an analysis result by using image processing technology such as a neural network system that performs a computation by using an artificial intelligence (AI) technology, machine learning, or a computer-aided detection (CAD) system.

Hereinafter, an X-ray image processing method according to an embodiment which may obtain information about the information about each of a plurality of materials included in an object from an X-ray image and an X-ray image processing apparatus using the X-ray image processing method will be described with reference to the attached drawings.

The X-ray image processing apparatus according to an embodiment may exist in various forms. For example, the X-ray image processing apparatus according to an embodiment may be formed in a console or the workstation 180 of the X-ray apparatus 100 of FIG. 1.

As another example, the X-ray image processing apparatus according to an embodiment may be formed in a device or server separate from the X-ray apparatus 100. The device or server separate from the X-ray apparatus 100 may be referred to as an 'external device'. Examples of the external device may include the external server 151, the medical device 152, and the portable terminal 153 of FIG. 1, and the external device may receive an actual X-ray image through a wired/wireless communication network with the X-ray apparatus 100. For example, the X-ray image processing apparatus according to an embodiment may be formed in an analysis workstation, an external medical device, a picture archiving communication system (PACS) server, a PACS viewer, an external medical server, or a hospitable server.

Figure 2:
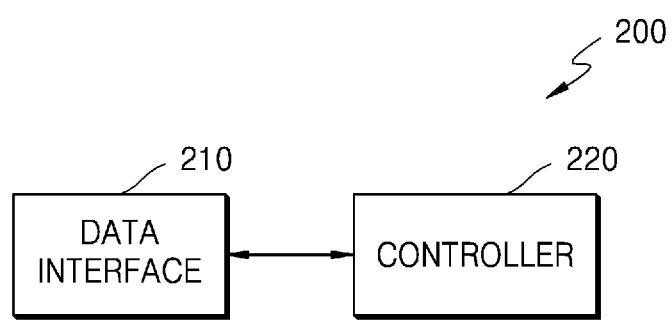
FIG. 2 is a block diagram illustrating an X-ray image processing apparatus according to an embodiment.

FIG. 2 is a block diagram illustrating an X-ray image processing apparatus according to an embodiment.

Referring to FIG. 2, an X-ray image processing apparatus 200 according to an embodiment may include a data interface 210 and a controller 220.

Also, when the X-ray image processing apparatus 200 is included in the X-ray apparatus 100 of FIG. 1, the controller 220 of FIG. 2 may correspond to the controller 120 of FIG. 1.

An X-ray image is an image obtained by projecting an X-ray to an object and imaging the inside of the object. Accordingly, the inside of the object is imaged in a superimposed manner in an X-ray emission direction. In detail, a plurality of materials included in the object in the X-ray image may be imaged in an overlapping manner. Accordingly, it was difficult to obtain information related to a stereoscopic structure of the inside of the object or a stereoscopic structure of each of the materials included in the object by using one X-ray image.

In an embodiment, information about each of a first material and a second material that are two different materials may be obtained by using one X-ray image (specifically, a first X-ray image).

The data interface 210 obtains the first X-ray image generated by imaging the object formed of a plurality of materials including the first material and the second material. The first material and the second material included in the object are different materials.

The object may be formed of a plurality of different materials. In detail, the object may be formed of body forming materials such as soft tissue, bones, and blood. Also, examples of the soft tissue may include muscles, fat, cartilage, fibrous tissue, and blood vessels.

In detail, the first material and the second material may be materials having different X-ray attenuation characteristics from among the materials included in the object. That is, the first material and the second material may have different X-ray attenuation coefficients.

The first X-ray image may be an X-ray image obtained by emitting an X-ray having a single energy band to the object. That is, the first X-ray image is one X-ray image corresponding to the single energy band.

In detail, the object may include a body part including at least one of cells, tissue, organs, or other body forming materials. In detail, the object may include a patient's arm, leg, abdomen, and/or breast. For example, materials included in the arm may be roughly divided into an arm bone and soft tissue surrounding the arm bone. For example, the first X-ray image may be an X-ray image obtained by emitting an X-ray having a single energy band to a body part of the patient formed of a bone and soft tissue such as an arm and performing imaging by using the X-ray transmitted and detected through the body part of the patient.

The controller 220 includes at least one processor that executes at least one instruction. The controller 220 controls the following operations to be performed by executing the at least one instruction. In detail, the controller 220 obtains a first partial image generated by imaging the first material and a second partial image generated by imaging the first material and the second material in an overlapping manner from the first X-ray image, by executing the at least one instruction. The controller 220 obtains first information related to a stereoscopic structure of the first material based on the first partial image included in the first X-ray image and obtains second information about the second material based on the first information and the second partial image.

In detail, the first partial image is a region where only the first material in the first X-ray image is imaged. The second partial image is a region where the first material and the second material in the first X-ray image are imaged in an overlapping manner.

In an embodiment, the first material may be soft tissue. The second material may be a bone. That is, according to an embodiment, the first information related to the stereoscopic structure of the first material may be obtained and then the second information about the second material may be obtained by using the first X-ray image that is one X-ray image.

Information related to a stereoscopic structure may be information necessary to three-dimensionally represent an object or at least one material of the object, instead of information that may be recognized from a two-dimensional (2D) image showing the object or the at least one material of the object.

In detail, the first information may include information about a thickness, a volume, a shape, a geometric structure, etc. of the object and/or at least one material of the object.

The second information may include information related to a stereoscopic structure of the second material. In detail, the second information may include information about a thickness, a volume, a shape, a geometric structure, etc. of the second material.

In an embodiment, a process of obtaining each of the first information about the first material and the second information about the second material may be referred to as 'material decomposition'.

In an embodiment, the controller 220 may segment a region where only the first material is imaged as the first partial image, and may segment a region where the first material and the second material are imaged in an overlapping manner as the second partial image.

In detail, segmentation or extraction of the first partial image and the second partial image may be performed based on intensity values of an X-ray transmitted through the object. In detail, segmentation or extraction of the first partial image and the second partial image may be performed based on intensity values of an X-ray detected by, for example, an X-ray detector 313 (see FIG. 3) to capture the first X-ray image. Alternatively, segmentation or extraction of the first partial image and the second partial image may be performed based on pixel values of the first X-ray image.

For example, the controller 220 may extract a region imaged with pixel values corresponding to intensity values of an X-ray transmitted through the first material in the first X-ray image as the first partial image. Also, the controller 220 may obtain the second partial image adjacent to the first partial image and corresponding to a boundary between a region where the first material exists and a region where the first material and the second material exist in an overlapping manner. In detail, the first partial image and the second partial image may be images adjacent to each other at a boundary between the first material and the second material. That is, the first partial image includes a region where only the first material is imaged at the boundary between the first material and the second material. The second partial image includes a region where the first material and the second material are imaged in an overlapping manner, at the boundary between the first material and the second material.

In detail, the controller 220 may obtain the first information from the first partial image by using X-ray absorption characteristics. The X-ray absorption characteristics refer to characteristics in which at least a part of an X-ray output (or emitted) to the object is absorbed by a material in the object, and only at least a part of the output X-ray passes through the object and is detected. Because the output X-ray is attenuated while passing through the object, the X-ray absorption characteristics may be referred to as X-ray attenuation characteristics.

Also, the controller 220 may obtain the second information from the second partial image by using the X-ray absorption characteristics and the first information.

A configuration of obtaining at least one of the first information or the second information based on the X-ray absorption characteristics will be described in detail with reference to FIGS. 5 through 8.

Also, the data interface 210 may obtain the first X-ray image by using various methods. For example, when the X-ray image processing apparatus 200 is formed inside a medical imaging apparatus (e.g., the X-ray apparatus 100), the X-ray image processing apparatus 200 itself may obtain an X-ray image by performing X-ray imaging. As another example, when the X-ray image processing apparatus 200 is formed separately from the medical imaging apparatus (e.g., the X-ray apparatus 100), the X-ray image processing apparatus 200 may receive an X-ray image through a wired/wireless communication network from the medical imaging apparatus. In this case, the data interface 210 may include thereinside a communicator (e.g., a communicator 415 of FIG. 4, not shown in FIG. 2), and may receive the first X-ray image through the communicator provided inside the data interface 210.

An operation and a configuration in which the data interface 210 itself obtains an X-ray image by performing X-ray imaging will be described in detail with reference to FIG. 3.

Also, the controller 220 includes at least one processor that executes one or more instructions. Each of the at least one processor may perform a predetermined operation by executing at least one of the one or more instructions.

Also, the controller 220 may include an internal memory and at least one processor that executes at least one stored program. In detail, the internal memory of the controller 220 may store one or more instructions. The at least one processor included in the controller 220 may perform a predetermined operation by executing at least one of one or more instructions stored in the internal memory of the controller 220.

In detail, the controller 220 may include a random-access memory (RAM) for storing signals or data input from the outside of the X-ray image processing apparatus 200 or used as a storage corresponding to various tasks performed by the X-ray image processing apparatus 200, a read-only memory (ROM) for storing a plurality of instructions and/or a control program for controlling the X-ray image processing apparatus 200, and at least one processor. The processor may include a graphics processing unit (GPU) for performing graphics processing on a video. The processor may be implemented as a system-on-chip (SoC) in which a core is combined with a GPU. The processor may include a single-core, a dual-core, a triple-core, a quad-core, and a multiple core thereof.

Also, the at least one processor included in the controller 220 may control operations performed by the X-ray image processing apparatus 200, and may control other elements included in the X-ray image processing apparatus 200 to perform a predetermined operation. Accordingly, although the controller 220 is described as controlling predetermined operations to be performed, it will be understood that the at least one processor included in the controller 220 controls the predetermined operations to be performed.

Figure 3:
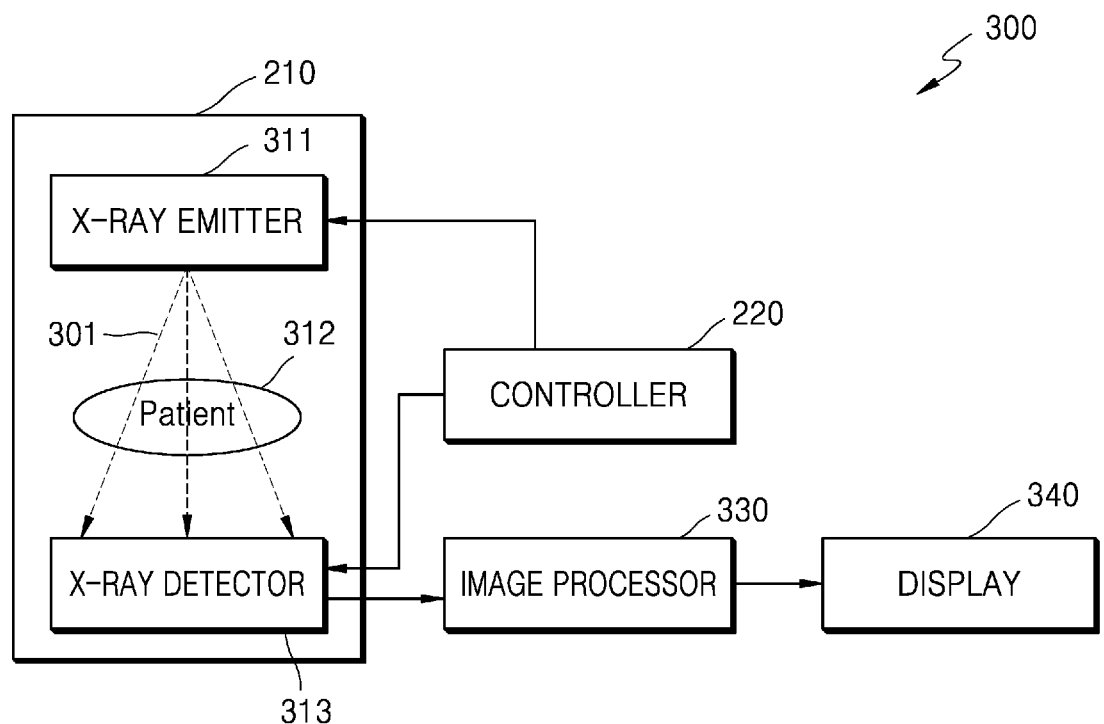
FIG. 3 is a block diagram illustrating an X-ray image processing apparatus according to another embodiment.

FIG. 3 is a block diagram illustrating an X-ray image processing apparatus according to another embodiment. The same elements of an X-ray image processing apparatus 300 of FIG. 3 as those of the X-ray image processing apparatus 200 of FIG. 2 are denoted by the same reference numerals. Hence, the same description of the X-ray image processing apparatus 300 of FIG. 3 as that made with reference to FIG. 2 will be omitted.

A data interface 210 may include an X-ray emitter 311 that performs X-ray imaging by emitting an X-ray to an object 312 and an X-ray detector 313. The object 312 may be a body part of a patient. For example, when a musculoskeletal system from among body parts of the patient needs to be diagnosed, the object 312 to which an X-ray is to be emitted may be the patient's shoulder, arm, or leg.

Also, because the X-ray emitter 311 and the X-ray detector 313 of FIG. 3 respectively correspond to the X-ray emitter 110 and the X-ray detector 195 of FIG. 1, the same description as that made with reference to FIG. 1 will be omitted.

The X-ray emitter 311 generates an X-ray and emits the X-ray to the object 312. In detail, the X-ray emitter 311 may generate an X-ray by applying a high voltage between a cathode and an anode of a vacuum tube included in the X-ray emitter 311. An intensity of an X-ray output from the X-ray emitter 311 may vary according to a tube voltage applied to the vacuum tube, tube current, and a product specification (e.g., a size of a filament, a size of a focusing electrode, a distance between the anode and the cathode) of the vacuum tube. Also, because the tube voltage applied to generate the X-ray and the product specification of the vacuum tube have set values or determined values, the intensity of the X-ray output from the X-ray emitter 311 has a known value or a measurable value.

In an embodiment, the X-ray emitter 311 may emit an X-ray having a single energy band to the object 312.

The X-ray detector 313 detects the X-ray emitted from the X-ray emitter 311 and transmitted through the object. In detail, the X-ray output from the X-ray emitter 311 may be attenuated while passing through the object 312.

The X-ray detector 313 may detect the attenuated X-ray, and the controller 220 may control an image processor 330 to generate a first X-ray image based on an X-ray detection result of the X-ray detector 313. Also, an intensity of the X-ray passing through the object 312 may be obtained based on the number of X-ray photons detected by the X-ray detector 313.

The image processor 330 generates an X-ray image based on the X-ray detection result of the X-ray detector 313 under the control of the controller 220. In detail, the X-ray detected by the X-ray detector 313 is converted into an electrical signal. The image processor 330 may generate the X-ray image based on the converted signal. That is, a pixel value of the X-ray image may correspond to a size of the electrical signal converted from the X-ray detected by the X-ray detector 313. Also, the image processor 330 may perform pre-processing on the signal generated according to the X-ray detection result of the X-ray detector 313 and may perform post-processing for improving the quality of the X-ray image. Also, types and an order of image processing operations performed by the image processor 330 may be changed.

A display 340 displays a predetermined screen under the control of the controller 220. In detail, the display 340 may display at last one of the first X-ray image, first information, or second information. Also, the display 340 may display at least one of a first partial image or a second partial image. Also, the display 340 may display a user interface screen including at least one of the first X-ray image, the first partial image, the second partial image, the first information, or the second information.

Figure 4:
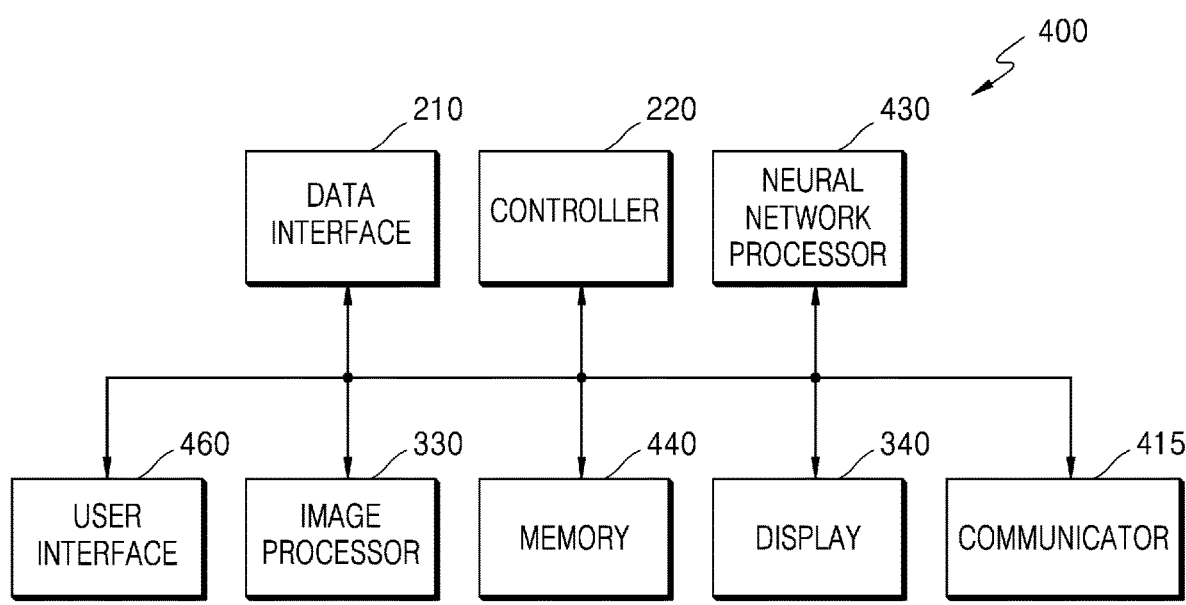
FIG. 4 is a block diagram illustrating an X-ray image processing apparatus according to another embodiment.

FIG. 4 is a block diagram illustrating an X-ray image processing apparatus according to another embodiment. The same elements of an X-ray image processing apparatus 400 of FIG. 4 as those of the X-ray image processing apparatuses 200 and 300 of FIGS. 2 and 3 are denoted by the same reference numerals. Hence, the same description of the X-ray image processing apparatus 400 as that made with reference to FIGS. 2 and 3 will be omitted.

The X-ray image processing apparatus 400 may further include at least one of a neural network processor 430, a user interface 460, the image processor 330, a memory 440, a display 340, or a communicator 415, when compared to the X-ray image processing apparatus 200.

Also, the controller 220 may obtain a first partial image and a second partial image included in a first X-ray image through machine learning. In detail, the machine learning may be performed by using an AI system according to AI technology, data-based statistical machine learning, or a CAD operation that detects or segments the first partial image and the second partial image from the first X-ray image through a computer operation.

In detail, by using AI technology, an operation for obtaining the first partial image and the second partial image may be performed through a computation via a neural network. The neural network may optimize and set weight values inside the neural network by training using training data. The neural network self-learns input data in order to derive a result value to be obtained.

In detail, the neural network may be a deep neural network (DNN). Also, a DNN computation may include a convolutional neural network (CNN) computation. In detail, a data recognition model may be implemented through the neural network, and may be trained by using training data. Input data, e.g., an X-ray image, may be analyzed and classified by using the trained data recognition model, and a specific region or a specific partial image (e.g., the first partial image and the second partial image) included in the X-ray image may be analyzed and classified.

In an embodiment, the controller 220 may obtain the first partial image and the second partial image from the first X-ray image by performing a computation through a neural network.

Also, the computation through the neural network may be performed by the neural network processor 430 that is a separate processor. Also, the computation through the neural network may be performed by using at least one of at least one processor included in the controller 220. In FIG. 4, the computation through the neural network is performed by the neural network processor 430 that is a processor separate from the controller 220.

The neural network processor 430 may perform a computation based on the neural network. In detail, a DNN computation may include a CNN computation.

In detail, the neural network processor 430 may obtain the first partial image and the second partial image from the first X-ray image by performing the computation through the neural network. The neural network computation performed by the neural network processor 430 or the controller 220 will be described in detail with reference to FIG. 9.

The communicator 415 may transmit/receive data to/from an electronic device through a wired/wireless communication network. In detail, the communicator 415 may transmit/receive data under the control of the controller 220. The communicator 415 may correspond to the communicator 140 of FIG. 1. Also, the electronic device connected through the wired/wireless communication network to the communicator 415 may be the external server 151, the medical device 152, or the portable terminal 153 of FIG. 1. Also, the electronic device may be a medical imaging apparatus, e.g., the X-ray apparatus of FIG. 1, which is formed separately from the X-ray image processing apparatus 300.

In detail, when an external electronic device is a medical imaging apparatus, the communicator 415 may receive an actual medical image, e.g., the first X-ray image, obtained by the medical imaging apparatus. Also, the communicator 415 may transmit, to the external electronic device, at least one medical image and/or data including a result obtained by analyzing or diagnosing the medical image. For example, when the controller 220 obtains first information and second information, the controller 220 may transmit information obtained through the communicator 415 to the external electronic device.

The memory 440 may include at least one program necessary to operate the X-ray image processing apparatus 300 or at least one instruction necessary to execute the at least one program. Also, the memory 440 may include one or more processors for performing the above operations.

Also, the memory 440 may store at least one of the X-ray image, information related to the X-ray image, information about a patient, information about an object, or information about an examinee. Also, the memory 440 may store at least one of information, data, or an image generated by the controller 220 or the neural network processor 430. Also, the memory 440 may store at least one of an image, data, or information received from the external electronic device.

The display 340 may display a medical image, a user interface screen, user information, image processing information, etc. In detail, the display 340 may display the user interface screen generated under the control of the controller 220. The user interface screen may include the X-ray image, the information related to the X-ray image, and/or information generated by the controller 220 or the neural network processor 430.

The user interface 460 may receive predetermined data or a predetermined command from a user. The user interface 460 may correspond to at least one of the sub-user interface 80 or the input interface 181 of FIG. 1. Also, the user interface 460 may be formed as a touchscreen that is integrally formed with the display 340. As another example, the user interface 460 may include a user input device such as a pointer, a mouse, or a keyboard.

Figure 5:
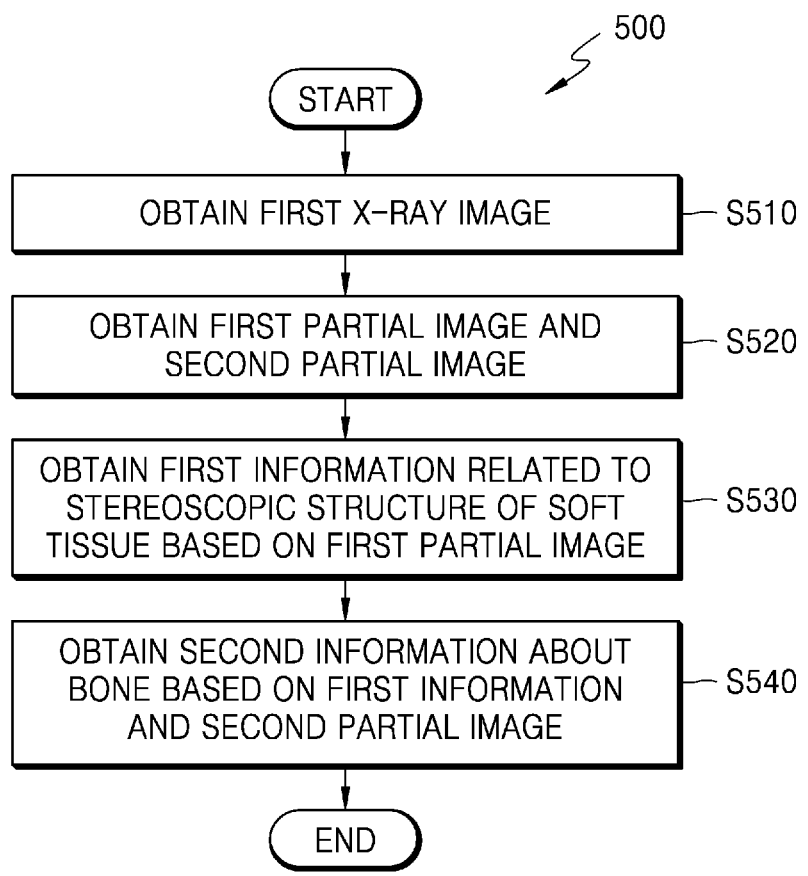
FIG. 5 is a flowchart illustrating an X-ray image processing method according to an embodiment.

FIG. 5 is a flowchart illustrating an X-ray image processing method according to an embodiment. An X-ray image processing method 500 according to an embodiment may be performed by the X-ray image processing apparatus 200, 300, or 400 according to an embodiment with reference to FIGS. 2 through 4. Accordingly, each operation of the X-ray image processing method 500 may be performed by each element of the X-ray image processing apparatus 200, 300, or 400, and the X-ray image processing method 500 may have the same characteristics as those of the X-ray image processing apparatus 200, 300, or 400. That is, FIG. 5 may be a view illustrating operations performed by the X-ray image processing apparatus 200, 300, or 400 according to an embodiment. Accordingly, the same description of the X-ray image processing method 500 as that made with reference to FIGS. 1 through 4 will be omitted.

The X-ray image processing method 500 will be described in detail with reference to the X-ray image processing apparatus 200 of FIG. 2.

Referring to FIG. 5, in operation S510, the X-ray image processing method 500 obtains a first X-ray image. The first X-ray image is an X-ray image obtained by imaging an object formed of a plurality of materials including a first material and a second material. Operation S510 may be performed by the data interface 210 under the control of the controller 220.

In operation S520, a first partial image obtained by imaging the first material and a second partial image obtained by imaging the first material and the second material in an overlapping manner are obtained from the first X-ray image. Operation S520 may be performed by the controller 220.

Operations S510 and S520 will be described in detail with reference to FIGS. 6 and 7.

Figure 6:
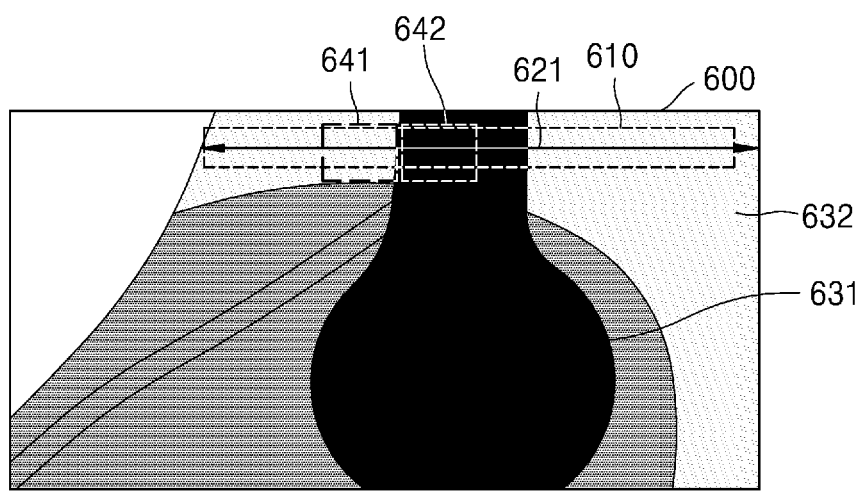
FIG. 6 is a view illustrating an X-ray image obtained according to an embodiment.

FIG. 6 is a view illustrating an X-ray image obtained according to an embodiment.

Referring to FIG. 6, an X-ray image 600 obtained by imaging a patient's shoulder in order to diagnose a musculoskeletal disorder of the patient is illustrated. In the X-ray image 600, a bone 631 is the brightest, and soft tissue 632 adjacent to the bone 631 and surrounding the bone 631 is darker than the bone 631. Also, a part corresponding to an X-ray passing through the object without being transmitted through the object may be imaged in black in the X-ray image 600.

The following will be described assuming that the first material is the soft tissue 632 and the second material is the bone 631. In the following equations, 'S' denotes soft tissue, and 'B' denotes a bone.

In an embodiment, in operation S520, the controller 220 obtains a first partial image (e.g., a region 641) generated by imaging only the soft tissue 632 in the first X-ray image (e.g., the X-ray image 600) and a second partial image (e.g., a region 642) generated by imaging the soft tissue 632 and the bone 631 in an overlapping manner. The first partial image includes the region 641 generated by imaging only the first material at a boundary between the soft tissue 632 that is the first material and the bone 631 that is the second material. The second partial image includes the region 641 where the soft tissue 632 that is the first material and the bone 631 that is the second material are imaged in an overlapping manner at the boundary between the soft tissue 632 that is the first material and the bone 631 that is the second material. Because the bone 631 is surrounded by the soft tissue 632 such as skin or muscles, a region where the bone 631 is imaged may be referred to as a region where the bone 631 and the soft tissue 632 are imaged in an overlapping manner.

In detail, the controller 220 may segment or extract a region (e.g., the region 641) generated with only pixel values corresponding to soft tissue from the first X-ray image as the first partial image, based on pixel values of the first X-ray image. Alternatively, the controller 220 may segment or extract a region (e.g., the region 641) generated with only pixel values corresponding to soft tissue from the first X-ray image as the first partial image, based on intensity values of an X-ray detected by the X-ray detector 313 (see FIG. 3) to capture the first X-ray image. The controller 220 may segment or extract a region (e.g., the region 642) adjacent to the first partial image, located at a boundary between the soft tissue and a bone, and generated by imaging the bone and the soft tissue in an overlapping manner as the second partial image. In detail, the first partial image and the second partial image may indicate regions adjacent to each other at the boundary between the bone and the soft tissue in the first X-ray image.

Next, in operation S530, the X-ray image processing method 500 obtains first information related to a stereoscopic structure of the first material based on the first partial image (e.g., the region 641) included in the first X-ray image (e.g., the X-ray image 600). Operation S530 may be performed by the controller 220. The first information may include information related to the stereoscopic structure of the first material, e.g., information about a thickness, a volume, a shape, a geometric structure, etc.

In operation S540, the X-ray image processing method 500 obtains second information about the second material based on the first information obtained in operation S530 and the second partial image (e.g., the region 642). Operation S540 may be performed by the controller 220. The second information may include information related to a stereoscopic structure of the second material. In detail, the second information may include information about a thickness, a volume, a shape, a geometric structure, etc. of the second material.

The controller 220 may obtain the first information from the first partial image by using X-ray absorption characteristics. Also, the controller 220 may obtain the second information from the second partial image by using the X-ray absorption characteristics and the first information.

An operation of obtaining first information will be first described and then an operation of obtaining second information will be described, with reference to FIGS. 7 and 8.

Figure 7:
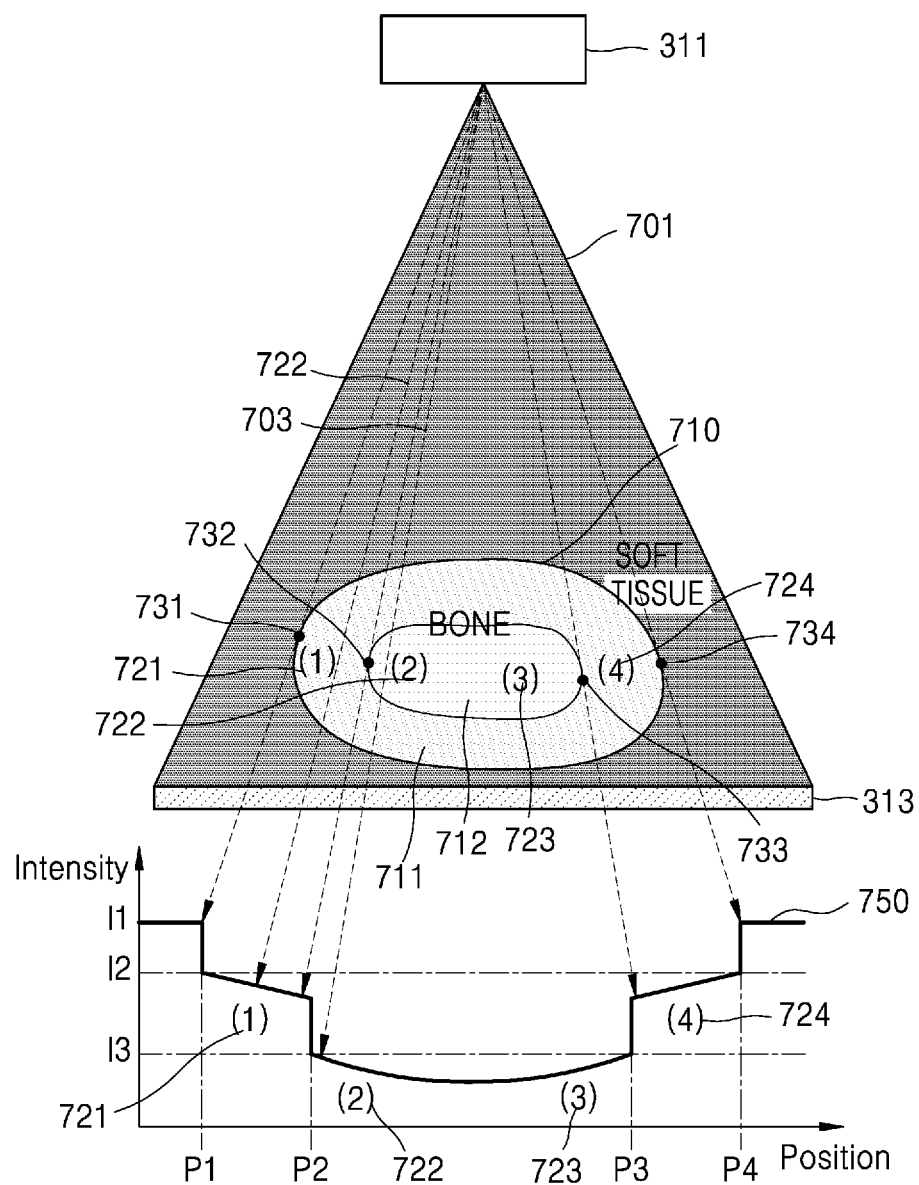
FIG. 7 is a view for describing an operation of obtaining an X-ray image according to an embodiment.

FIG. 7 is a view for describing an operation of obtaining an X-ray image according to an embodiment. The same elements in FIG. 7 as those of FIG. 3 are denoted by the same reference numerals. Accordingly, the same description of FIG. 7 as that made with reference to FIG. 3 will be omitted.

Referring to FIG. 7, an X-ray 701 is emitted to an object 710 to obtain a first X-ray image. In detail, the X-ray emitter 311 outputs an X-ray having an intensity $I_o$ to the object 710. The X-ray detector 313 detects an X-ray having an intensity I that is an X-ray passing through the object 710. The first X-ray image may be generated based on the X-ray detected by the X-ray detector 313. In FIG. 7, a bone 712 and soft tissue 711 may respectively correspond to the bone 631 and the soft tissue 632 of FIG. 6. FIG. 7 may illustrate a cross-section of the object 710 in a depth direction of a perpendicular line 621 of FIG. 6.

In FIG. 7, the object 710 includes the bone 712 and the soft tissue 711 surrounding the bone 712, for convenience of description. For example, the object 710 may be an arm or a leg. Also, FIG. 7 illustrates a vertical cross-section of the object 710 in an X-ray emission direction.

Referring to FIG. 7, a graph 750 is a graph showing an intensity of an X-ray detected by the X-ray detector 313. In detail, the X-axis of the graph 750 represents a position in the vertical cross-section of the object 710, and the Y-axis represents an intensity of the X-ray detected by the X-ray detector 313. In detail, that is, the X-axis of the graph 750 may correspond to the perpendicular line 621 of FIG. 6.

Also, the Y-axis of the graph 750 may represent the intensity I of the X-ray transmitted through the object 710.

Referring to FIG. 750, an intensity of an X-ray not transmitted through the object may be I1. The intensity I1 may be the same as the intensity $I_o$ of the X-ray emitted by the X-ray emitter 311. The intensity of the X-ray transmitted through the object 710 starts to be reduced from the boundary 731 of the object 710. For example, the intensity of the X-ray detected by the X-ray detector 313 is reduced from I1 at the boundary 731 of the object 710 to I2. In the graph 750, a position corresponding to the boundary 731 of the object 710 is denoted by P1. The reduction in the intensity of the X-ray occurs because a part of the X-ray is absorbed by the object 710 while being transmitted through the object 710. Such X-ray absorption characteristics may be referred to as X-ray attenuation characteristics.

The X-ray absorption characteristics may vary according to internal materials of the object 710. For example, X-ray attenuation when passing through the bone 712 may be greater than X-ray attenuation when passing through the soft tissue 711. Also, as a thickness of the object 710 through which the X-ray is transmitted increases, X-ray attenuation may increase. Also, as internal materials change, a degree of X-ray absorption or attenuation also changes.

Referring to FIG. 7, a region 721 (1) of the object 710 is a region where only the soft tissue 711 exists. A region 722 (2) and a region 723 (3) of the object 710 are regions where the soft tissue 711 and the bone 712 exist in an overlapping manner and an X-ray 703 output from the X-ray emitter 311 is transmitted through both the bone 712 and the soft tissue 711. A region 724 (4) of the object 710 is a region where only the soft tissue 711 exists.

An X-ray 702 transmitted through the region 721 (1) of the object 710 may have the same intensity as that in an interval between the position P1 and a position P2 of the graph 750. A degree of X-ray absorption or attenuation at the boundary 732 between the soft tissue 711 and the bone 712 sharply changes. In the graph 750, a position corresponding to the boundary 732 between the soft tissue 711 and the bone 712 is denoted by P2. Accordingly, an X-ray transmitted through the bone 712 and detected may have the same intensity as that in an interval between the position P2 and a position P3.

Also, a degree of X-ray absorption or attenuation at a boundary 733 between the bone 712 and the soft tissue 711 sharply changes. In the graph 750, a position corresponding to the boundary 733 between the bone 712 and the soft tissue 711 is denoted by P3. Accordingly, an X-ray transmitted through the soft tissue 711 and detected may have the same intensity as that in an interval between the position P3 and a position P4.

In detail, X-ray absorption characteristics may be defined as in [Equation 1].

$$I = I_o e^{-\Sigma(\mu_j(E) \times t_j)} \quad \text{[Equation 1]}$$

I denotes an intensity of an X-ray transmitted through an object and detected, $I_o$ denotes an intensity of an X-ray emitted to the object (i.e., an intensity of an X-ray generated by the X-ray emitter 311 and output to the object 312), and $\mu_j(E)$ denotes an attenuation coefficient indicating a degree to which an X-ray having an energy band E is attenuated while being transmitted through a j material. The attenuation coefficient may vary according to a material. For example, attenuation coefficients of soft tissue and a bone have different values. $t_j$ denotes a thickness of the j material. Because the intensities I and $I_o$ respectively correspond to the X-ray transmitted through the object and detected and the X-ray output to the object during. X-ray imaging, the intensities I and $I_o$ may be immediately known as a result of setting and X-ray detection during the X-ray imaging of the X-ray apparatus 100.

In detail, the intensity I may be a signal value generated by electrically converting the number of X-ray photons detected by the X-ray detector 313. For example, the intensity I may be a voltage value generated by electrically converting the number of X-ray photons detected by the X-ray detector 313. Alternatively, the intensity I may be a current value generated by electrically converting the number of X-ray photons detected by the X-ray detector 313.

Also, the intensities I and $I_o$ may be obtained by using corresponding pixel values in an X-ray image. That is, the intensity I may correspond to a pixel value of a designated region in the X-ray image, and the intensity $I_o$ may correspond to a pixel value corresponding to an output X-ray, that is, a pixel value of a region where the object does not exist in the X-ray image. Also, a pixel value of the X-ray image may be represented as a value obtained by inverting a value corresponding to the number of X-ray photons detected by the X-ray detector 313 (see FIG. 3). For example, when an X-ray passes through the bone and attenuation of the X-ray increases, the number of X-ray photons passing through the bone decreases. However, because a value of the X-ray image is represented as a value obtained by inverting a value corresponding to the number of detected X-ray photons, the bone in the X-ray image may be represented with a brighter pixel value than other materials, for example, the soft tissue. As another example, attenuation of the X-ray passing through the soft tissue is less than attenuation of the X-ray passing through the bone. In this case, the soft tissue in the X-ray image may be represented with a darker pixel value than the bone. Hence, an intensity of a corresponding X-ray may be obtained by using a pixel value in the X-ray image.

In an embodiment, a first partial region where only the soft tissue is imaged may correspond to the region 721 (1), and a second partial region where the soft tissue and the bone are imaged in an overlapping manner may correspond to the region 722 (2).

Also, [Equation 1] may be modified to [Equation 2].

$$J = -\log\left[\frac{I}{Io}\right] = \sum (\mu_j(E) \times t_j) \quad \text{[Equation 2]}$$

Also, when an X-ray passes through an object (e.g., a specific body part of a patient) existing in a three-dimensional (3D) space, a degree of X-ray attenuation is proportional to a density of a material existing in the space, and thus $\mu_j(E)$ may be represented as $\mu_j \rho_j$. $\rho_j$ denotes a density value of a j material. That is, when the X-ray passes through the object having a 3D structure, a degree of X-ray attenuation may be represented as a value obtained by multiplying an attenuation coefficient of the j material by a density of the j material. Accordingly, [Equation 1] may be modified to [Equation 3].

$$I = I_o e^{-\Sigma(\mu_j \rho_j \times t_j)} \quad \text{[Equation 3]}$$

Each of [Equation 1] through [Equation 3] is represented using a sigma that is a summation of $\mu_j(E) \times t_j$ that is a value obtained by multiplying $\mu_j(E)$ by $t_j$. This indicates that when an X-ray is transmitted through a plurality of materials that exist in an overlapping manner, the X-ray is attenuated inversely exponentially with respect to a value obtained by adding $\mu_j(E) \times t_j$ values of the plurality of materials.

As described above, it is assumed that the first material is the soft tissue and the second material is the bone. In this case, for the first partial image generated by imaging only the soft tissue that is the first material, [Equation 2] is represented as [Equation 4]. For the second partial image generated by imaging the soft tissue that is the first material and the bone that is the second material in an overlapping manner, [Equation 2] is represented as [Equation 5].

$$J = -\log\left[\frac{I}{Io}\right] = \mu_S \rho_S t_S \quad \text{[Equation 4]}$$

$$J = -\log\left[\frac{I}{Io}\right] = \mu_S \rho_S t_S + \mu_B \rho_B t_B \quad \text{[Equation 5]}$$

In [Equation 4], S denotes values of the soft tissue, and B denotes values of the bone. In [Equation 5], an attenuation coefficient $\mu_S$ of the soft tissue, a density $\rho_S$ of the soft tissue, an attenuation coefficient $\mu_B$ of the bone, and a density $\rho_B$ of the bone may be known values. $t_S$ denotes a thickness of the soft tissue, and $t_B$ denotes a thickness of the bone.

Hence, when values measured or obtained in the first, partial image (e.g., the region 721 (1) of FIG. 7) generated by imaging only the soft tissue are applied to [Equation 4], $t_s$ that is the thickness of the soft tissue in the first partial image may be obtained.

In detail, because a thickness, a density, and an attenuation coefficient of the soft tissue 711 in [Equation 5] are known and $I_o$ is known, $t_B$ that is the thickness of the bone may be obtained by using [Equation 5] indicating X-ray absorption characteristics. I in [Equation 5] may be an intensity value of an X-ray that is transmitted through a portion of the object 710 where the bone and the soft tissue overlap and is detected. Accordingly, I may have a measured value, and the measured value may be applied to [Equation 5].

When the first partial image and the second partial image are adjacent at a boundary (e.g., the boundary 732) between the bone and the soft tissue, a thickness of the soft tissue imaged in the second partial image may be obtained based on a thickness of the soft tissue imaged in the first partial image.

Figure 8:
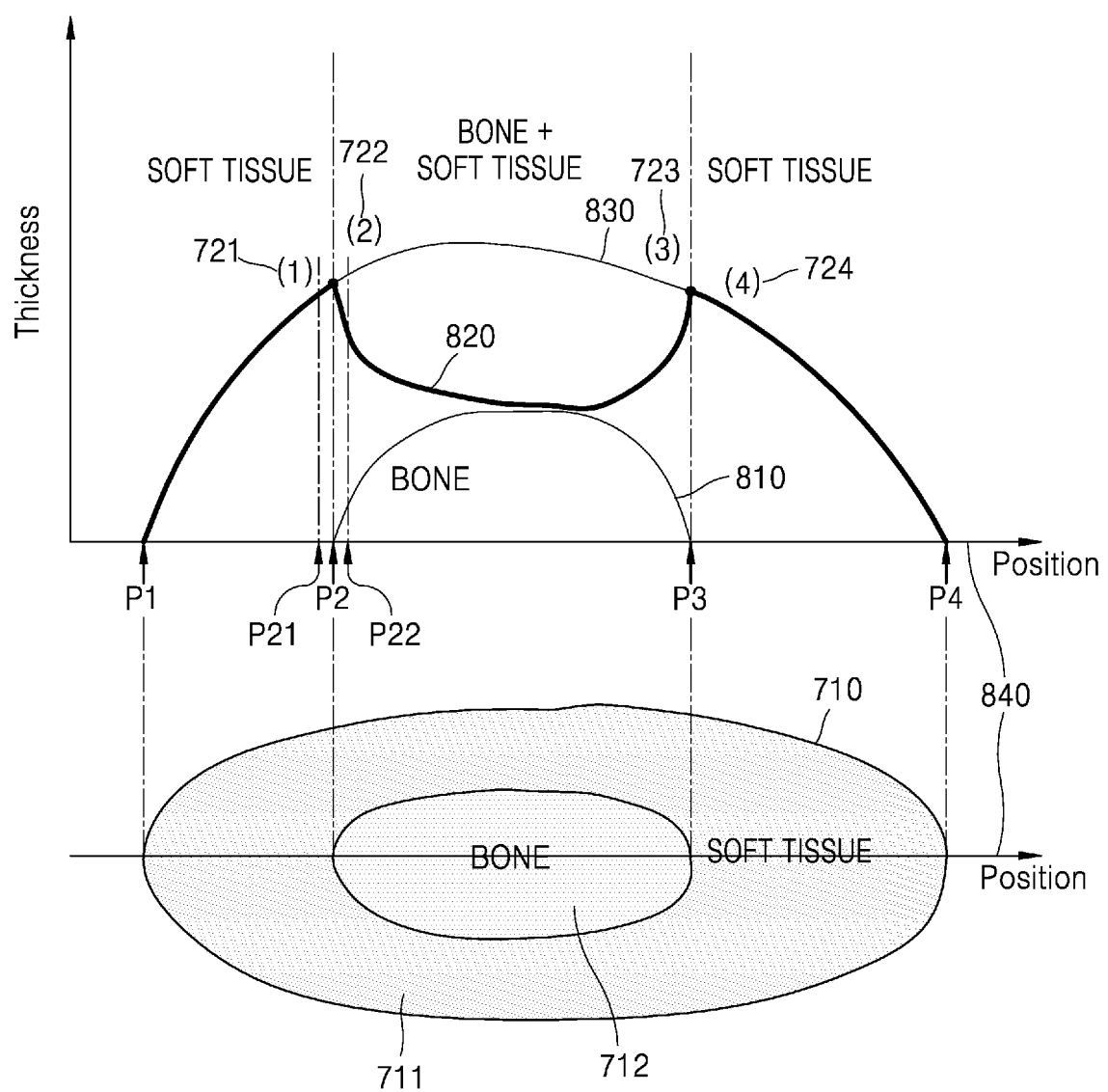
FIG. 8 is a view for describing thicknesses of materials in an object imaged in an X-ray image.

FIG. 8 is a view for describing thicknesses of materials in an object imaged in an X-ray image. In FIG. 8, the same elements as those of FIG. 7 are denoted by the same reference numerals. Graphs 800 of FIG. 8 are graphs for describing a thickness of an object in a vertical cross-section of the object along a predetermined axis (e.g., the perpendicular line 621 of FIG. 6). The X-axis 840 of FIG. 8 may correspond to the X-axis of the graph 750 of FIG. 7. The Y-axis of the graphs 800 of FIG. 8 represents thicknesses of materials included in the object 710.

Referring to FIG. 8, a graph 820 shows a thickness of soft tissue, and a graph 810 shows a thickness of a bone. The graph 830 shows a thickness of the object 710 including the bone and the soft tissue.

Referring to FIGS. 7 and 8, in the object 710, only the soft tissue 711 exists in the interval between the position P1 corresponding to the boundary 731 of the object 710 and the position P2 corresponding to the boundary 732 between the soft tissue 711 and the bone 712, and a thickness of the soft tissue 711 in the interval between the positions P1 and P2 gradually increases. A thickness of the soft tissue 711 in the interval between the positions P1 and P2 may be obtained by using X-ray absorption characteristics, specifically, [Equation 4].

Next, a thickness of the bone 712 may start to increase as shown in the graph 810 from the boundary 732 between the soft tissue 711 and the bone 712.

Thicknesses of the soft tissue 711 at two adjacent positions P21 and P22 based on the boundary 732 between the soft tissue 711 and the bone 712 may have the same value or similar values. In detail, because a distribution of the soft tissue 711 is continuous, a distribution of the soft tissue 711 at the boundary 732 between the soft tissue 711 and the bone 712 is continuous. That is, a thickness of the soft tissue 711 and a thickness of the object 710 do not start to sharply change but start to smoothly change from the boundary 732 between the soft tissue 711 and the bone 712. As such, total thickness distribution characteristics of materials included in a human body may be represented as shown in the graph 830 of FIG. 8. The total thickness distribution characteristics of the materials included in the human body may be referred to as a smooth thickness shift principle.

Also, the total thickness distribution characteristics may have a known shape obtained based on a diagnosis result of a plurality of patients. That is, the graph 830 of FIG. 8 may have a shape that is experimentally or statistically known. Also, the graph 830 of FIG. 8 may be modeled through a human body model or a human body profile based on a thickness distribution measurement result of the plurality of patients.

Accordingly, when a thickness of the soft tissue 711 at the position P2 or P21 corresponding to the boundary 732 between the soft tissue 711 and the bone 712 is known, a thickness of the soft tissue 711 imaged in the second partial region adjacent to the boundary 732 between the soft tissue 711 and the bone 712 may be known. Because the position P21 and the position P22 are adjacent to each other based on the position P2 corresponding to the boundary 732 between the soft tissue 711 and the bone 712, a total thickness of the object 710 at the position P21 and a total thickness of the object 710 at the position P22 continuously smoothly change.

That is, the controller 220 may obtain a thickness of the soft tissue 711 imaged in the second partial image, based on first information including a thickness of the soft tissue 711.

Because a thickness of the object 710 is continuous and a thickness of the soft tissue 711 is continuous as shown in the graph 830, it may be assumed that a total thickness of the object 710 measured at the position P21 is the same as a total thickness of the object 710 measured at the position P22.

Accordingly, [Equation 6] may be obtained.

$$t_{s1} = t_{s2} + t_{B2}$$ [Equation 6]

In [Equation 6], s1 denotes the soft tissue 711 existing in an object region imaged in the first partial image, s2 denotes the soft tissue 711 existing an object region imaged in the second partial image, and B2 denotes the bone 712 existing in an object region imaged in the second partial image. That is, $t_{s1}$ denotes a thickness of the soft tissue 711 imaged in the first partial image, $t_{s2}$ denotes a thickness of the soft tissue 711 imaged in the second partial image, and $t_{B2}$ denotes a thickness of the bone 712 imaged in the second partial image. Also, $t_{s1}$ denotes a thickness of the soft tissue 711 at the position P21 (position in the object 710 corresponding to the first partial image) adjacent to the boundary 732 between the soft tissue 711 and the bone 712, $t_{s2}$ denotes a thickness of the soft tissue 711 at the position P22 (position in the object 710 corresponding to the second partial image) adjacent to the boundary 732 between the soft tissue 711 and the bone 712, and $t_{B2}$ denotes a thickness of the bone 712 at the position P22 (position in the object 710 corresponding to the second partial image) adjacent to the boundary 732 between the soft tissue 711 and the bone 712.

As described above, when it is assumed that a total thickness of the object 710 measured at the position P21 is the same as a total thickness of the object 710 measured at the position P22, the thickness $t_{s1}$ of the soft tissue 711 that is a total thickness of the object 710 at the position P21 may be the same as a value obtained by summing the thickness $t_{s2}$ of the soft tissue 711 and the thickness $t_{B2}$ of the bone 712 measured at the position P22.

Also, [Equation 6] may be modified to [Equation 7].

$$t_{s2} = t_{s1} - t_{B2}$$ [Equation 7]

Also, in an object region corresponding to the second partial image where the soft tissue and the bone coexist, [Equation 5] may be represented as [Equation 8].

$$J = -\log\left[\frac{I}{I_o}\right] = \mu_S \rho_S t_{S2} + \mu_B \rho_B t_{B2}$$ [Equation 8]

In [Equation 8], an attenuation coefficient $\mu_S$ of the soft tissue, a density $\rho_S$ of the soft tissue, an attenuation coefficient $\mu^B$ of the bone, and a density $\rho_B$ of the bone may be known values. I in [Equation 8] is an intensity value of an X-ray that is transmitted through the object where the bone and the soft tissue coexist and is detected, and thus may be measured during X-ray imaging.

When [Equation 7] is applied to $t_{s2}$ in [Equation 8], [Equation 9] may be obtained.

$$J = -\log\left[\frac{I}{I_o}\right] = \mu_S \rho_S (t_{S1} - t_{B2}) + \mu_B \rho_B t_{B2}$$ [Equation 9]

[Equation 9] may be modified to [Equation 10].

$$J = -\log\left[\frac{I}{I_o}\right] = (\mu_B \rho_B - \mu_S \rho_S) t_{B2} + \mu_S \rho_S t_{S1}$$ [Equation 10]

In [Equation 10], an attenuation coefficient $\mu_S$ of the soft tissue, a density $\rho_S$ of the soft tissue, an attenuation coefficient $\mu_B$ of the bone, and a density $\rho_B$ of the bone are known values, and $t_{s1}$ is a value obtained by using [Equation 4] indicating X-ray absorption characteristics and the first partial image. I in [Equation 10] is an intensity value of an X-ray that is transmitted through the object where the bone and the soft tissue coexist and is detected, and thus may be measured during X-ray imaging. Hence, in [Equation 10], because all values except the thickness $t_{B2}$ of the bone in an object region corresponding to the second partial image may be assignable values, the thickness $t_{B2}$ may be obtained.

Once the thickness $t_{B2}$ is obtained, the thickness $t_{s2}$ of the soft tissue in an object region (specifically, an object region corresponding to the second partial image) where the bone and the soft tissue coexist may be obtained by applying the thickness $t_{B2}$ and the thickness $t_{s1}$ that is already obtained to [Equation 7].

As described above, in an embodiment, the controller 220 may obtain both a thickness of the bone and a thickness of the soft tissue in the second partial image.

By using the above method, in an entire region of the object in the X-ray image according to an embodiment, thicknesses of the soft tissue and the bone may be measured. According to an embodiment, information about a 3D distribution of the soft tissue and the bone included in the object may be obtained based on the thicknesses of the soft tissue and the bone. Also, according to an embodiment, volumes of the soft tissue and the bone may be obtained based on the thicknesses of the soft tissue and the bone.

In detail, the controller 220 may obtain third information stereoscopically showing a distribution of at least one of the soft tissue or the bone imaged in the first X-ray image, based on the first information and the second information. In detail, the third information may include at least one of a 3D geometric model of the soft tissue or a 3D geometric model of the bone. The term 'geometric model' may be information indicating at least one of a 3D shape, a volume, a density, or a configuration of a corresponding material.

As described above, a process of obtaining information about each of different materials included in the object may be referred to as material decomposition.

In a conventional X-ray image processing apparatus and a conventional X-ray image processing method, when an object is formed of a plurality of materials, in order to obtain information about each of the plurality of different materials included in the object, a plurality of X-ray images obtained by emitting X-rays corresponding to a plurality of energy bands to the object were required. This is because [Equation 1] showing X-ray absorption characteristics is represented using a sigma that is a summation of the plurality of materials included in the object. The X-rays corresponding to the plurality of energy bands may be referred to as dual energy X-rays or multi-energy X-rays.

For example, in the related art, in order to measure thicknesses of a bone and soft tissue, both an X-ray image obtained by emitting an X-ray having a low energy band to the object and an X-ray image obtained by emitting an X-ray having a high energy band to the object had to be used. Accordingly, in order to obtain thicknesses of the plurality of materials in the object, X-ray imaging had to be performed multiple times. Accordingly, the amount of X-rays emitted to a patient had to increase.

Also, in the related art, information about a stereoscopic structure of the object may not be obtained from one X-ray image having a single energy band. This is because due to X-ray image characteristics, the object may be two-dimensionally imaged by projecting an X-ray to a front surface of the object, and information about a vertical cross-section of the front surface of the object may not be obtained.

However, according to an embodiment, the first partial image generated by imaging only the first material and the second partial image generated by imaging the first material and the second material in an overlapping manner may be segmented or extracted from one X-ray image (e.g., the first X-ray image) and stereoscopic information about the first material (e.g., a thickness of the first material) and information about the second material may be obtained based on the extracted first partial image and the extracted second partial image. Accordingly, information of each of different materials may be obtained more rapidly and easily. Also, because only the first X-ray image is obtained through one X-ray imaging, the amount X-rays emitted to an object may be minimized.

Also, the first partial image and the second partial image may be obtained by using a computation through a neural network. The computation through the neural network may be performed by the controller 220 or the neural network processor 430. The computation through the neural network will be described in detail with reference to FIG. 9.

Also, the computation through the neural network may be performed in an external device (e.g., the external server 151, the medical device 152, or the portable terminal 153 (e.g., a smartphone, a tablet PC, or a wearable device)) connected through a wired or wireless network to the X-ray image processing apparatus 200. In this case, the X-ray image processing apparatus 200 may receive a result of the computation through the neural network, for example, the first partial image and the second partial image extracted or segmented in the first X-ray image, from the external device.

For convenience of explanation, the following will be described assuming that the computation through the neural network is performed by the controller 220.

Figure 9:
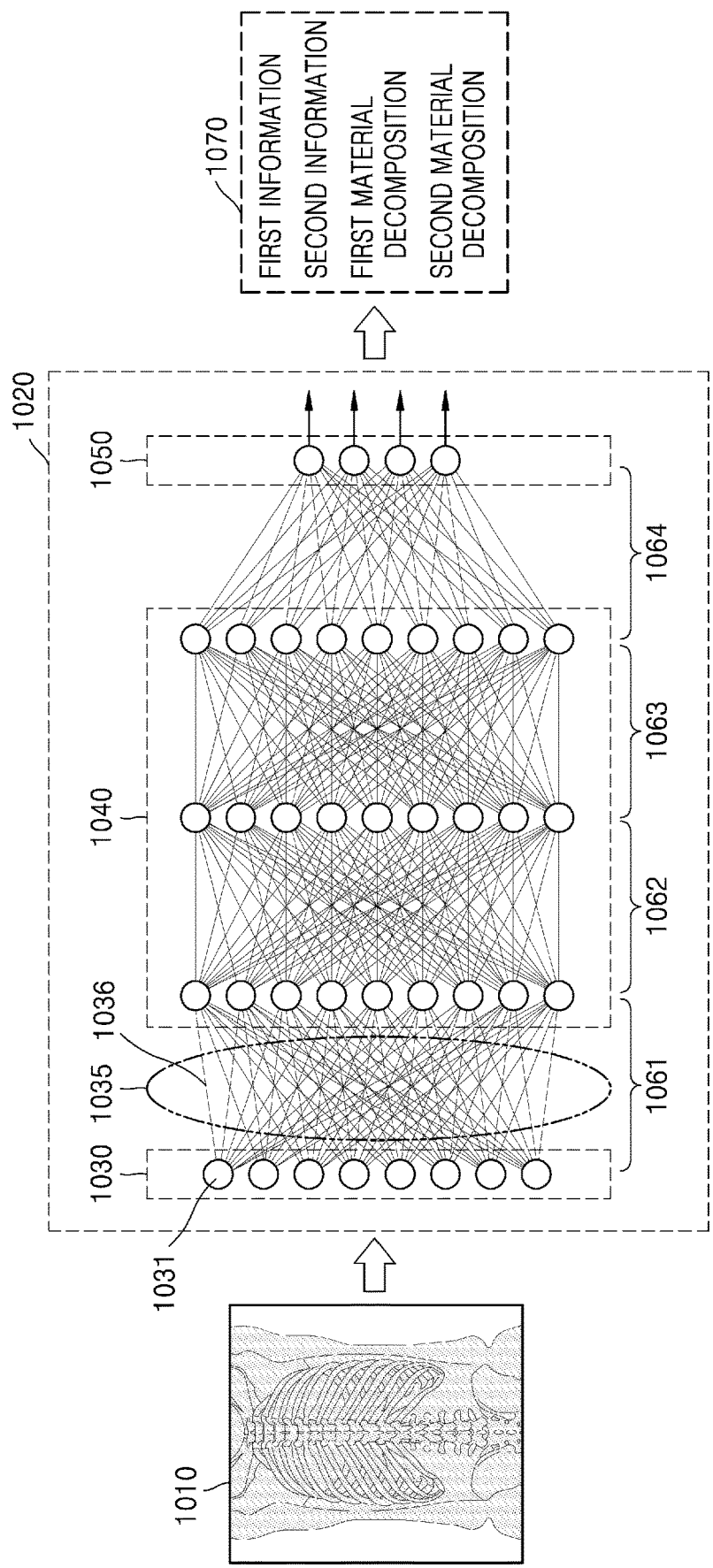
FIG. 9 is a view for describing a neural network through which a computation for obtaining a first partial region and a second partial region is performed.

FIG. 9 is a view for describing a neural network performing operations for obtaining a first partial region and a second partial region.

The controller 220 may perform a computation through a neural network, e.g., a Deep Neural Network (DNN) 1020, including an input layer, a hidden layer, and an output layer. In FIG. 9, a DNN including hidden layers that are formed at multiple levels is illustrated.

Referring to FIG. 9, the DNN 1020 includes an input layer 1030, a hidden layer 1040, and an output layer 1050. In FIG. 9, the DNN 1020 through which a computation is performed to analyze information included in a first X-ray image that is input data and to segment or extract a first partial image generated by imaging a first material and a second partial image generated by imaging the first material and a second material in an overlapping manner from the first X-ray image is illustrated. In detail, when input data is a first X-ray image 1010, the DNN 1020 may analyze an object to be imaged and included in the first X-ray image 1010, may extract the first partial image generated by imaging the first material and the second partial image generated by imaging the first material and the second material in an overlapping manner, and may output an extraction result as output data 1070.

The first X-ray image 1010 input to the input layer 1030 corresponds to a first X-ray image obtained in operation S510.

A plurality of layers included in the DNN 1020 may include a plurality of nodes (e.g., 1031) that receive data. Two adjacent layers are connected to each other through a plurality of edges (e.g., 1036). Each of the nodes has a corresponding weight value, and thus the DNN 1020 may obtain output data based on a value obtained by performing a computation, e.g., a convolution operation, on an input signal and a weight value.

The DNN may perform inference and estimation based on a neural network, and a DNN computation may include a CNN computation. That is, the DNN 1020 according to an embodiment may be implemented as a CNN that performs a CNN computation.

Referring to FIG. 9, the input layer 1030 receives the first X-ray image 1010 obtained by imaging the chest that is the object.

In FIG. 9, the hidden layer 1040 includes three-level layers. A depth of the hidden layer 1040 may vary according to order specifications and/or design specifications of a used neural network.

Referring to FIG. 9, the DNN 1020 may include a first layer 1061 formed between the input layer 1030 and a first hidden layer, a second layer 1062 formed between the first hidden layer and a second hidden layer, a third layer 1063 formed between the second hidden layer and a third hidden layer, and a fourth layer 1064 formed between the third hidden layer and the output layer 1050.

The plurality of nodes included in the input layer 1030 of the DNN 1020 receive a plurality of data corresponding to the first X-ray image 1010. The plurality of data may be a plurality of partial images generated by performing filter processing to segment the first X-ray image 1010.

Through a computation on a plurality of layers included in the hidden layer 1040, the output layer 1050 may output the output data 1070 obtained as a result of analyzing the first X-ray image 1010. The output data 1070 may include the first partial image generated by imaging the first material and the second partial image generated by imaging the first material and the second material in an overlapping manner.

In detail, when the DNN 1020 is implemented as a CNN and correlation among pieces of information included in an image is local, the CNN may introduce a filter applied only to a specific area, may perform convolution on pieces of information in the filter, and may precisely extract information about the feature of the image in the filter.

In detail, in the hidden layer 1040 existing in the DNN 1020 based on the CNN, a convolution layer and a pooling layer are alternately located and a depth of each layer filter increases from left to right. Also, a final end of the DNN 1020 based on the CNN may be implemented as a fully connected layer. The convolution layer is a layer of data generated according to a convolution operation, and the pooling layer is a layer for reducing the number or a size of data through an operation such as sub-sampling or pooling. Data (e.g., a feature map) indicating characteristics of an input image is generated while passing through the convolution layer and the pooling layer. In detail, through a computation through the hidden layer 1040, image features of the first X-ray image 1010 may be generated, and the first partial image generated by imaging only the first material and the second partial image generated by imaging the first material and the second material in an overlapping manner may be more precisely extracted based on the image features.

When the data generated by passing through the convolution layer and the pooling layer is processed through a hidden layer implemented as a fully connected layer, the first partial image and the second partial image to be extracted or segmented may be extracted and output.

Also, in order to improve the accuracy of data output through the DNN 1020, training may be performed in a direction from the output layer 1050 to the input layer 1030 and weight values of the nodes (e.g., 1031) included in the DNN 1020 may be corrected to improve the precision of the output data. Accordingly, before the first X-ray image 1010 is input, the DNN 1020 may train a plurality of different X-ray images and may correct a weight value of each node in a direction in which the first partial image generated by imaging the first material included in the X-ray image and the second partial image generated by imaging the first material and the second material are accurately detected.

Also, the DNN 1020 may perform a computation for obtaining first information about a stereoscopic structure of the first material and second information about the second material based on the first partial image and the second partial image.

Also, the DNN 1020 may perform a computation for first material decomposition and second material decomposition based on the first information and the second information. The DNN 1020 may output a result of the computation through the output layer 1050.

Also, the DNN 1020 may obtain the first information about the stereoscopic structure of the first material and the second information about the second material based on the first partial image and the second partial image, and may perform a computation for generating a 3D model of the object in which a plurality of materials included in the object are three-dimensionally represented based on the obtained first information and the obtained second information. The DNN 1020 may output an image in which each of the plurality of materials is three-dimensionally represented as a result of the computation through the output layer 1050. In this case, the DNN 1020 may be implemented as a capsule neural network (capsnet). The capsnet may perform a computation to generate an image in which each of the plurality of materials is three-dimensionally represented as a new image based on information (e.g., the first information and the second information) obtained through a neural network computation. The capsnet that is developed by making up for a weak point of a CNN may be referred to as a CNN-based neural network.

Figure 10:
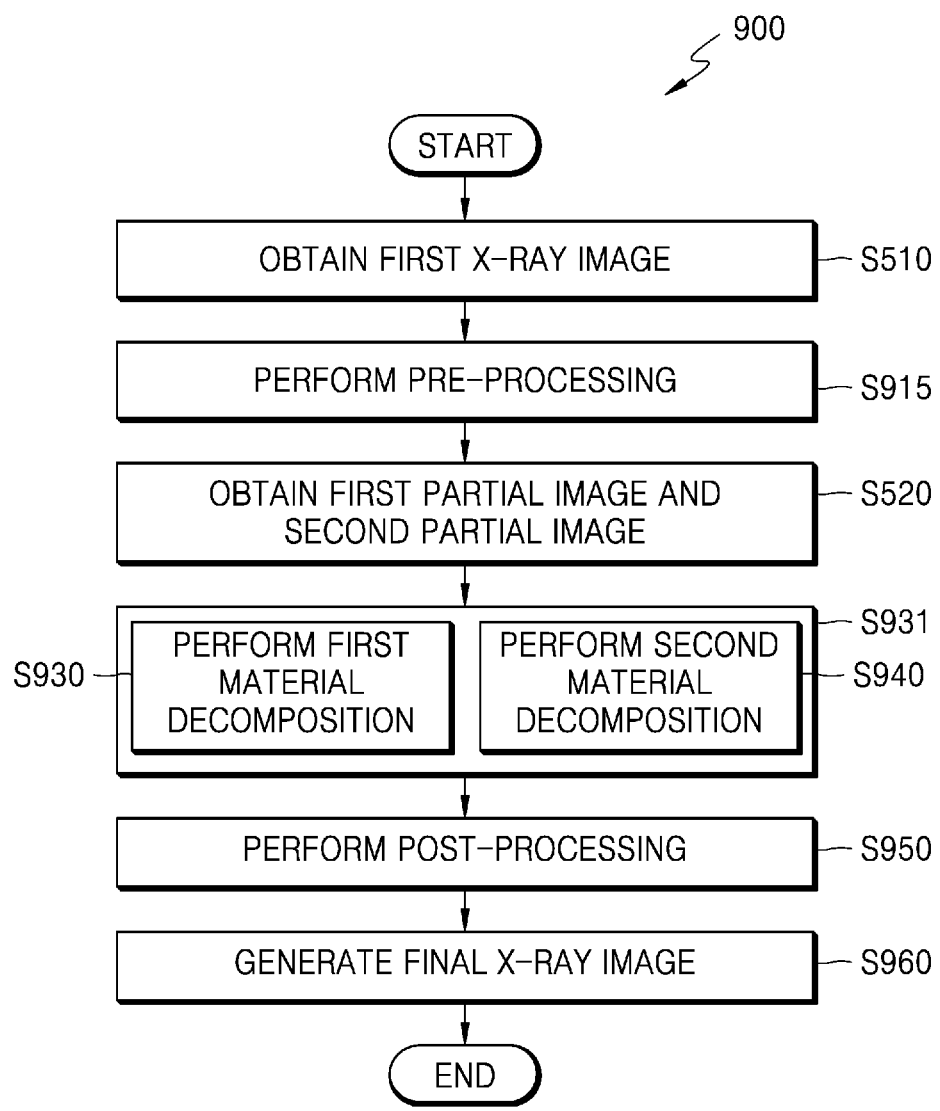
FIG. 10 is a flowchart illustrating an X-ray image processing method according to another embodiment.

FIG. 10 is a flowchart illustrating an X-ray image processing method according to another embodiment. An X-ray image processing method 900 according to an embodiment may be performed by the X-ray image processing apparatus 200, 300, or 400 according to an embodiment described with reference to FIGS. 2 through 4. Accordingly, each operation of the X-ray image processing method 900 may be performed by each element of the X-ray image processing apparatus 200, 300, or 400. Also, operations of the X-ray image processing method 900 may have the same characteristics as those of detailed operations of the X-ray image processing apparatus 200, 300, or 400 according to an embodiment described with reference to FIGS. 1 through 9.

Also, the same elements in the X-ray image processing method 900 of FIG. 10 as those of the X-ray image processing method 500 of FIG. 5 are denoted by the same reference numerals. Hence, the same description of the X-ray image processing method 900 as that made with reference to FIGS. 1 through 9 will be omitted.

The X-ray image processing method 500 will be described in detail with reference to the X-ray image processing apparatus 400 of FIG. 4.

The X-ray image processing method 900 may further include operation S915 in which pre-processing is performed on an X-ray image obtained in operation S510. Operation S915 may be performed by the image processor 330 under the control of the controller 220.

In detail, the pre-processing may include correction of signal intensity non-uniformity in a first X-ray image and improvement of a signal-to-noise ratio (SNR). That is, in operation S915, processing for correcting an image error such as signal non-uniformity in the first X-ray image may be performed to accurately extract a first partial image and a second partial image from the first X-ray image.

In operation S520, the first partial image and the second partial image are obtained based on the pre-processed first X-ray image.

In operation S931, first information and second information may be obtained by using the first partial image and the second partial image obtained in operation S520. Operation S931 may correspond to operations S530 and S540 of FIG. 5, and thus the same description as that made with reference to FIG. 5 will be omitted. Operation S931 may be performed by the controller 220.

In detail, in operation S931, material decomposition may be performed on a first material and a second material. The term 'material decomposition' may refer to a process of obtaining information about each of different materials included in an object.

In detail, in operation S930, the X-ray image processing method 900 may perform a first material decomposition operation of obtaining stereoscopic information about the first material. For example, information related to a stereoscopic structure of soft tissue that is the first material, e.g., information about a thickness, a volume, a shape, a geometric structure, etc., may be obtained.

In operation S940, the X-ray image processing method 900 may perform a second material decomposition operation of obtaining stereoscopic information about the second material. For example, information related to a stereoscopic structure of a bone that is the second material, e.g., information about a thickness, a volume, a shape, a geometric structure, etc., may be obtained.

A process of obtaining the first information and the second information has already been described in detail with reference to FIGS. 6 through 8 and the above equations, and thus a detailed explanation thereof will be omitted.

Also, the X-ray image processing method 900 may further include operation S950 in which post-processing is performed on at least one of the first X-ray image, the first partial image, or the second partial image. Operation S950 may be performed by the image processor 330 under the control of the controller 220.

The post-processing may include removal of a noise component included in an image (e.g., at least one of the first X-ray image, the first partial image, or the second partial image) to improve reading accuracy. For example, the post-processing may include removal or reduction of scattering noise caused by a scattered X-ray generated during X-ray imaging.

Next, in operation S960, the X-ray image processing method 900 generates a final X-ray image on which a post-processing result is reflected. Operation S960 may be performed by the image processor 330 under the control of the controller 220. The final X-ray image may be obtained by removing a noise component included in at least one of the first X-ray image, the first partial image, or the second partial image.

Also, the controller 220 may control the final X-ray image to be displayed on the display 340. Also, the controller 220 may control a user interface screen including at least one of the final X-ray image, the first information, or the second information to be displayed on the display 340.

Figure 11:
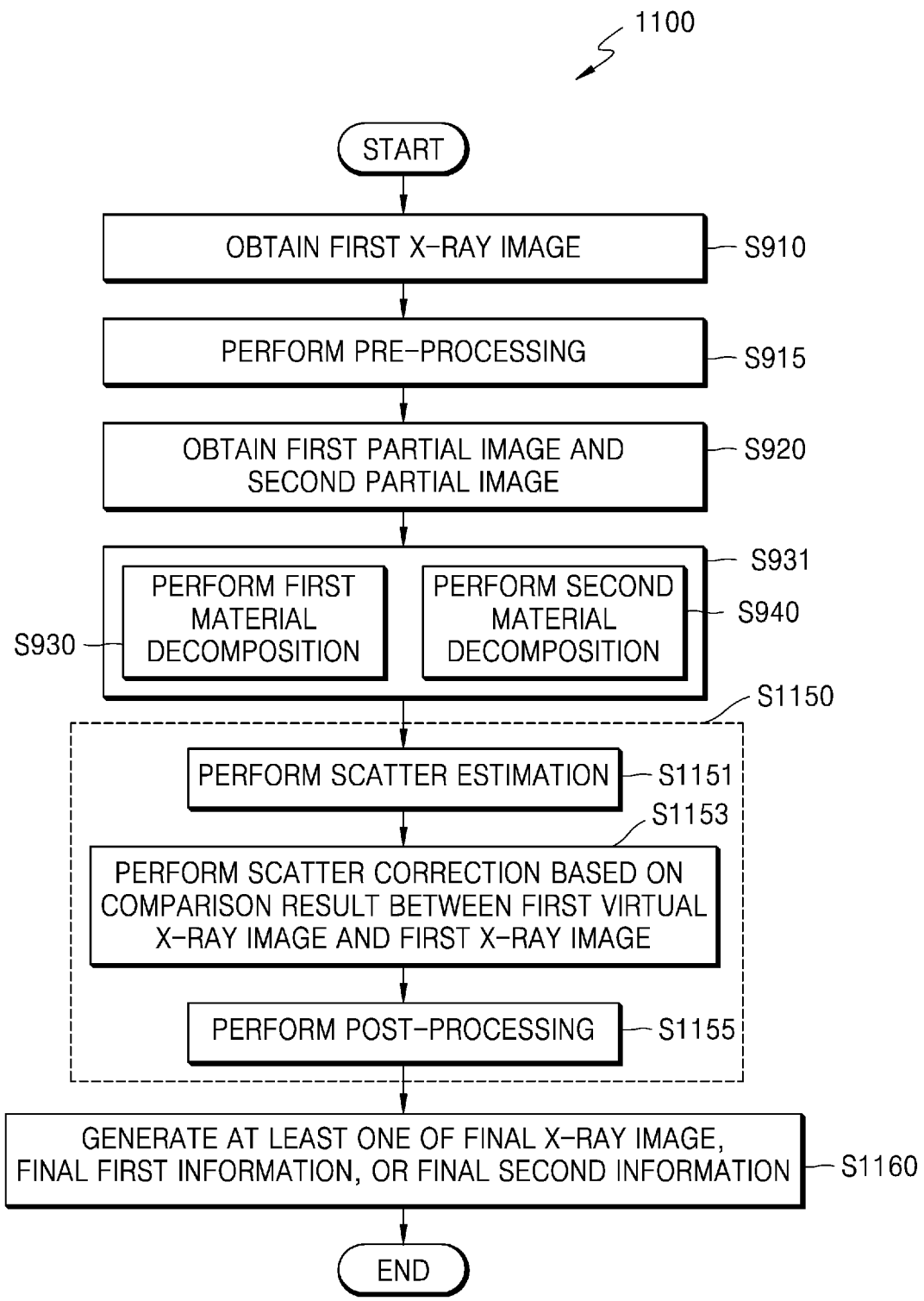
FIG. 11 is a flowchart illustrating an X-ray image processing method according to another embodiment.

FIG. 11 is a flowchart illustrating an X-ray image processing method according to another embodiment. Also, the same elements in an X-ray image processing method 1100 of FIG. 11 as those of the X-ray image processing method 900 of FIG. 10 are denoted by the same reference numerals. Hence, the same description of the X-ray image processing method 1100 as that made with reference to FIGS. 1 through 10 will be omitted.

The X-ray image processing method 1100 may perform scatter correction as post-processing on at least one of a first X-ray image, a first partial image, or a second partial image.

The term 'scatter correction' refers to a process of removing or reducing scattering noise caused by a scattered X-ray generated during X-ray imaging.

When the X-ray emitter 311 emits an X-ray to an object and the X-ray collides with the object, a scattered X-ray is generated. A part of the scattered X-ray is reflected inside and/or outside the object and spreads inside the object and/or in a space where the object is located. The scattered X-ray causes noise in an X-ray image, thereby reducing the quality of the X-ray image.

As described with reference to FIGS. 1 through 10, according to an embodiment, first information and second information may be accurately obtained when a first partial image and a second partial image are accurately extracted from the first X-ray image.

Accordingly, in order to accurately obtain the first information and the second information, the first X-ray image has to be an image in which the object is accurately imaged. Accordingly, image quality needs to be improved by removing a noise component in the first X-ray image. Hence, according to an embodiment, the first information and the second information may be accurately obtained by performing scatter correction.

Referring to FIG. 11, the X-ray image processing method 1100 may perform operation S1150 for scatter correction, after operation S931. Operation S1150 may be performed by the controller 220. Alternatively, operation S1150 may be performed by the image processor 330 under the control of the controller 220.

In detail, the controller 220 may perform scatter correction on the first X-ray image based on the first information and the second information, and may update the first information and the second information based on the scatter-corrected first X-ray image.

Once X-ray scattering occurs, a degree of scattering and scattering characteristics of materials included in a human body that is the object are changed. Accordingly, it is difficult to estimate a scattered X-ray without accurately decomposing the materials of the human body.

Accordingly, after the materials of the object are decomposed, the scattered X-ray may be estimated or predicted based on the decomposed materials. Hence, the X-ray image processing method 1100 may perform operation S931 in which a plurality of different materials included in the object, e.g., the first material and the second material, are decomposed, and then may perform operation S1151 in which a scattered X-ray is estimated based on the decomposed first material and second material. In operation S1153, the X-ray image processing method 1100 may perform scatter correction on the first X-ray image or the first partial image and the second partial image based on the estimated scattered X-ray.

Also, the X-ray image processing method 1100 may further include operation S1155 in which post-processing is performed on the scatter-corrected first X-ray image or the scatter-corrected first partial image and second partial image. Operation S1155 may be performed by the image processor 330 under the control of the controller 220. The post-processing corresponds to post-processing of operation S950 of FIG. 10, and thus a detailed explanation thereof will be omitted.

Next, in operation S1160, the X-ray image processing method 1100 may obtain at least one of a final X-ray image, final first information, or final second information, based on the scatter-corrected first X-ray image, or the scatter-corrected first partial image and second partial image. Operation S1160 may be performed by the controller 220. Alternatively, operation S1160 may be performed by the image processor 330 under the control of the controller 220.

In detail, the controller 220 may obtain the scatter-corrected first X-ray image as the final X-ray image. Alternatively, the controller 220 may re-obtain the first partial image and the second partial image from the scatter-corrected first X-ray image. The controller 220 may re-obtain the first information and the second information based on the re-obtained first partial image and second partial image. For convenience of explanation, the re-obtained first X-ray image, first information, and second information may be respectively referred to as the final first X-ray image, the final first information, and the final second information.

Also, the controller 220 may obtain the final first information and the final second information based on the scatter-corrected first partial image and second partial image.

Scatter correction will be described in detail with reference to FIGS. 12 and 13.

Figure 12:
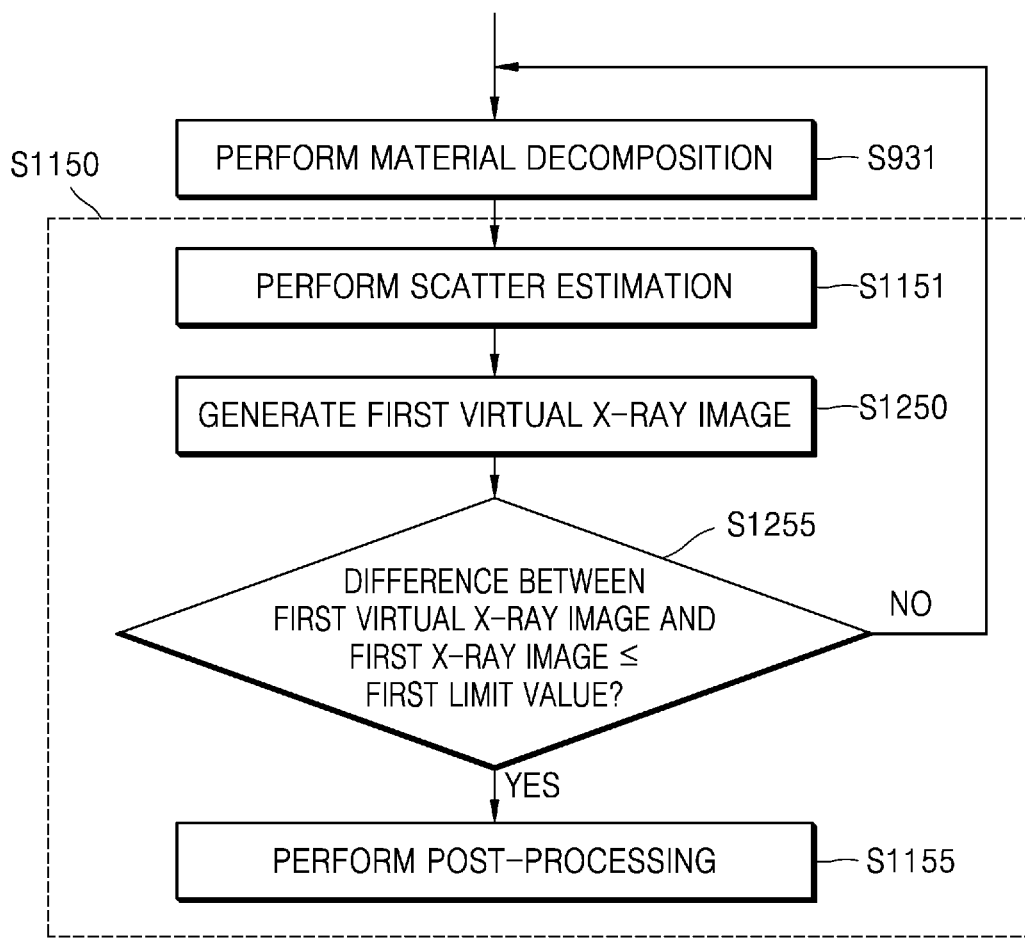
FIG. 12 is a diagram for describing a scatter correction operation according to an embodiment.

FIG. 12 is a diagram for describing a scatter correction operation according to an embodiment.

Figure 13:
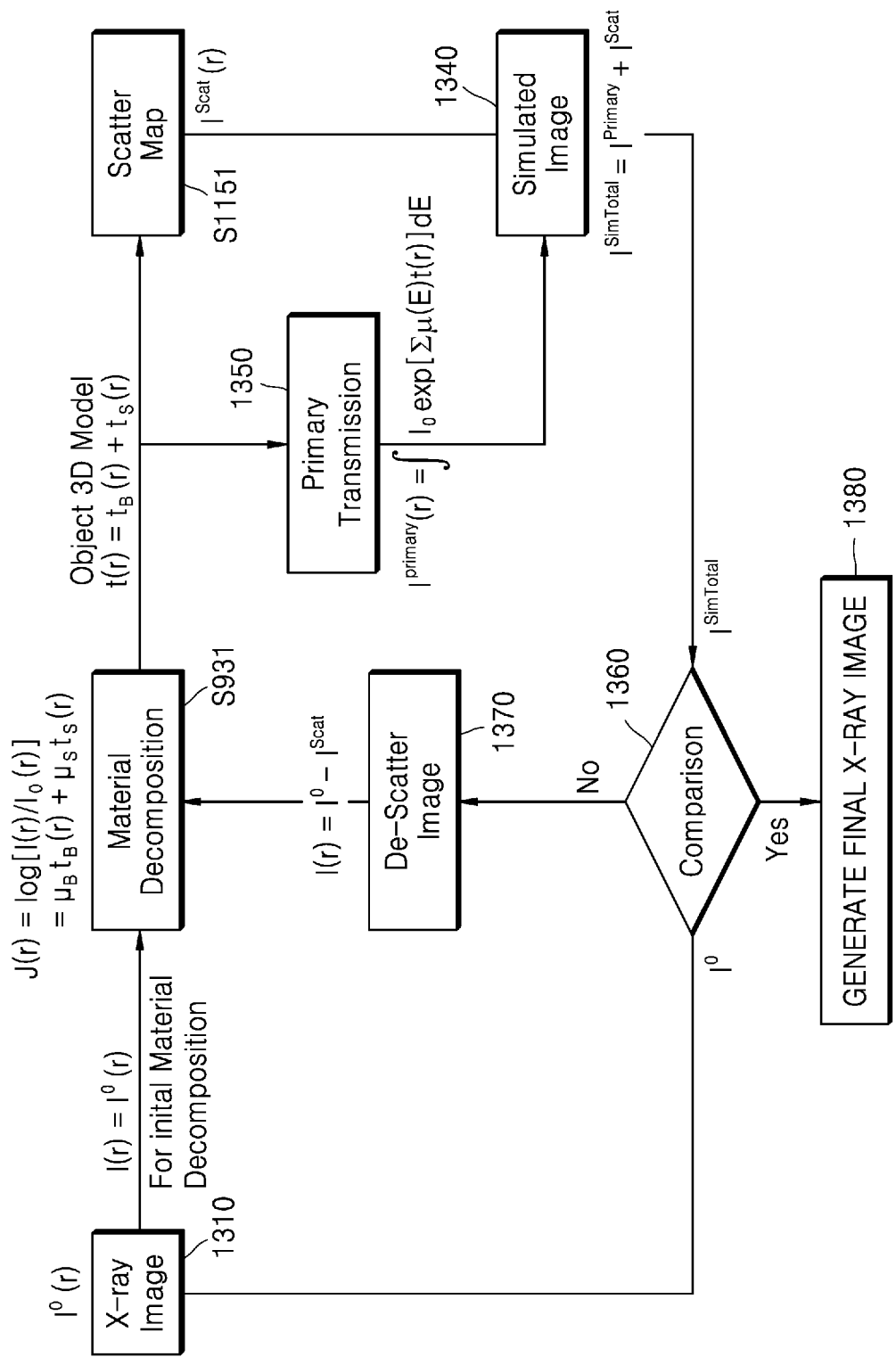
FIG. 13 is a diagram for describing a scatter correction operation according to another embodiment.

FIG. 13 is a diagram for describing a scatter correction operation according to another embodiment.

In operations of FIGS. 12 and 13, the same elements as those of FIGS. 10 and 11 are denoted by the same reference numerals. Hence, the same description of elements of FIGS. 12 and 13 as that made with reference to FIGS. 10 and 11 will be omitted.

Referring to FIG. 12, after operation S931 in which material decomposition of decomposing a first material and a second material that are different materials included in an object and obtaining information about the first material and the second material is performed, operation S1151 in which a scattered X-ray is estimated based on information obtained by the material decomposition, e.g., first information and second information, may be performed. A process of estimating the scattered X-ray generated during X-ray imaging of obtaining a first X-ray image is referred to as 'scatter estimation'.

Referring to FIG. 13, an X-ray image 1310 indicates a first X-ray image. In FIG. 13, $I^0(r)$ denotes an actual image obtained through X-ray imaging, that is, a first X-ray image before scatter correction. $I_o$ denotes an intensity of an X-ray emitted to an object (i.e., an intensity of an X-ray generated by the X-ray emitter 311 and output to the object 312) as in [Equation 1]. I(r) denotes a first X-ray image that is generated by updating. In detail, I(r) denotes an X-ray image that is generated by scatter correction. 'r' may denote a position corresponding to a pixel r (or an $r^{th}$ pixel) in a region of the object to be imaged. That is, I(r) may indicate an intensity of an X-ray detected at the position corresponding to the pixel r (or the $r^{th}$ pixel). Alternatively, I(r) may correspond to an image value (or a pixel value) of the pixel r (or the $r^{th}$ pixel) of the first X-ray image.

Also, I(r) in FIG. 13 denotes an X-ray image generated by performing scatter correction on the first X-ray image. Before scatter correction is performed, $I^0(r)$ and I(r) may be the same.

Also, variables in equations of FIG. 13 are the same as variables in [Equation 1] through [Equation 10], and thus a detailed explanation thereof will be omitted.

Referring to FIG. 13, operation S1151 that is a scatter estimation operation may be performed based on first information and second information. In detail, in operation S1151, a scatter map corresponding to a scattered X-ray in a first X-ray image may be generated based on the first information and the second information.

Referring to FIG. 13, the X-ray image processing method 1100 may obtain $I^{Scat}(r)$ that is a scatter map by performing operation S1151.

In detail, a first material (e.g., soft tissue) is decomposed and a second material (e.g., a bone) is decomposed in a first partial image and a second partial image segmented from the first X-ray image 1310. The scatter map may be generated by using t(r) that is a thickness distribution of the decomposed materials.

In detail, when a thickness distribution of a first material and a thickness distribution of a second material are known, how X-ray scattering occurs inside and/or outside the object may be estimated according to a density, an attenuation coefficient, a volume, etc. that are characteristics of each of the first material and the second material. The scatter map indicates a distribution of a scattered X-ray in an X-ray image. In detail, the scatter map may indicate a scattered X-ray generated inside and/or outside the object imaged in the first X-ray image and may be expressed as 2D information.

In operation S1155, post-processing of removing a noise component corresponding to the scattered X-ray in the first X-ray image may be performed by using the scatter map generated through scatter estimation. Operation S1155 may be performed by the controller 220. Alternatively, operation S1155 may be performed by the image processor 330 under the control of the controller 220.

In detail, a scatter-corrected first X-ray image may be generated by removing a scattered X-ray component included in the scatter map in the first X-ray image 1310. For example, the scattered X-ray image component may be removed from the first X-ray image 1310 by subtracting the scatter map from the first X-ray image 1310. The scatter-corrected first X-ray image is illustrated as a de-scatter image 1370 and is denoted by I(r). In detail, I(r) that is the scatter-corrected first X-ray image may be defined as in [Equation 11].

$$I(r) = I^0(r) - I^{Scat}(r) \quad \text{[Equation 11]}$$

Also, in operation S1250, the X-ray image processing method 1100 may generate a first virtual X-ray image, and in operations S1255 and S1155, the X-ray image processing method 1100 may perform scatter correction based on a comparison result between the first virtual X-ray image and the first X-ray image. Operations S1120, S1255, and S1155 may be performed by the controller 220. Alternatively, operations S1120, S1255, and S1155 may be performed by the image processor 330 under the control of the controller 220. The first virtual X-ray image is a simulated image 1340 generated based on the first information, the second information, and the scatter map.

In detail, referring to FIG. 12, in operation S931, materials included in an object are decomposed by performing material decomposition in operation, and first information and second information indicating a 3D structure of the decomposed materials are obtained. In detail, when the first information and the second information respectively include information about a thickness of a first material and information about a thickness of a second material, a 3D model of the object may be obtained by using the first information and the second information. Also, a phantom corresponding to the 3D model of the object may be generated based on the first information and the second information indicating the 3D structure of the decomposed materials. A primary image may be generated through a simulation operation of projecting an X-ray to the phantom. The transmission of the X-ray through the phantom corresponding to the 3D model of the object may be primary projection 1350. In operation S1250, when scattered radiation shown in the scatter map is added to the primary image, the first virtual X-ray image may be generated. Accordingly, the first virtual X-ray image may be defined as in [Equation 12].

$$I^{SimTotal}(r) = I^{Primary}(r) + I^{Scat}(r) \quad \text{[Equation 12]}$$

In [Equation 12], $I^{SimTotal}(r)$ denotes the first virtual X-ray image, and $I^{Primary}(r)$ denotes the primary image.

In operation S1255, the controller 220 may determine whether to update the scatter map based on a comparison result between the first virtual X-ray image and the first X-ray image 1310. Operation S1255 may be performed by the controller 220.

In detail, in operation S1155, when a difference value between the first virtual X-ray image and the first X-ray image is equal to or less than a first limit value, the controller 220 may perform post-processing of scatter correcting the first X-ray image, and in operation 1380, the controller 220 may generate a final X-ray image.

When a difference value between the first virtual X-ray image and the first X-ray image is greater than the first limit value, the controller 220 may return to operation S931 to update the scatter map, and may update the scatter map by re-performing operation S1151 that is a scatter estimation operation. When the scatter map is updated, the first X-ray image may be scatter corrected by using the previously obtained scatter map (i.e., the scatter map before updating), the first information and the second information may be re-obtained based on the scatter-corrected first X-ray image, and the scatter map may be re-obtained based on the re-obtained first information and second information. The re-obtained scatter map may be an updated scatter map. That is, as in [Equation 11], the scatter-corrected first X-ray image may be generated by subtracting a signal component in the scatter map from the first X-ray image. The scatter map may be updated by re-performing operation S931 that is a material decomposition operation and operation S1151 that is a scatter estimation operation based on the scatter-corrected first X-ray image.

In detail, the first limit value may be a reference value for comparing a similarity between the first X-ray image and the first virtual X-ray image. In detail, when a difference between the first X-ray image and the first virtual X-ray image and the first limit value are compared with each other, a value that allows the difference between the first X-ray image and the first virtual X-ray image to be within a set error range may be determined as the first limit value. The difference between the first X-ray image and the first virtual X-ray image may be expressed as a mean square value or the like. Also, the set error range may be set by the X-ray apparatus 100, the X-ray image processing apparatus 200, 300, or 400, or a user in consideration of target image quality of the first X-ray image.

Figure 14:
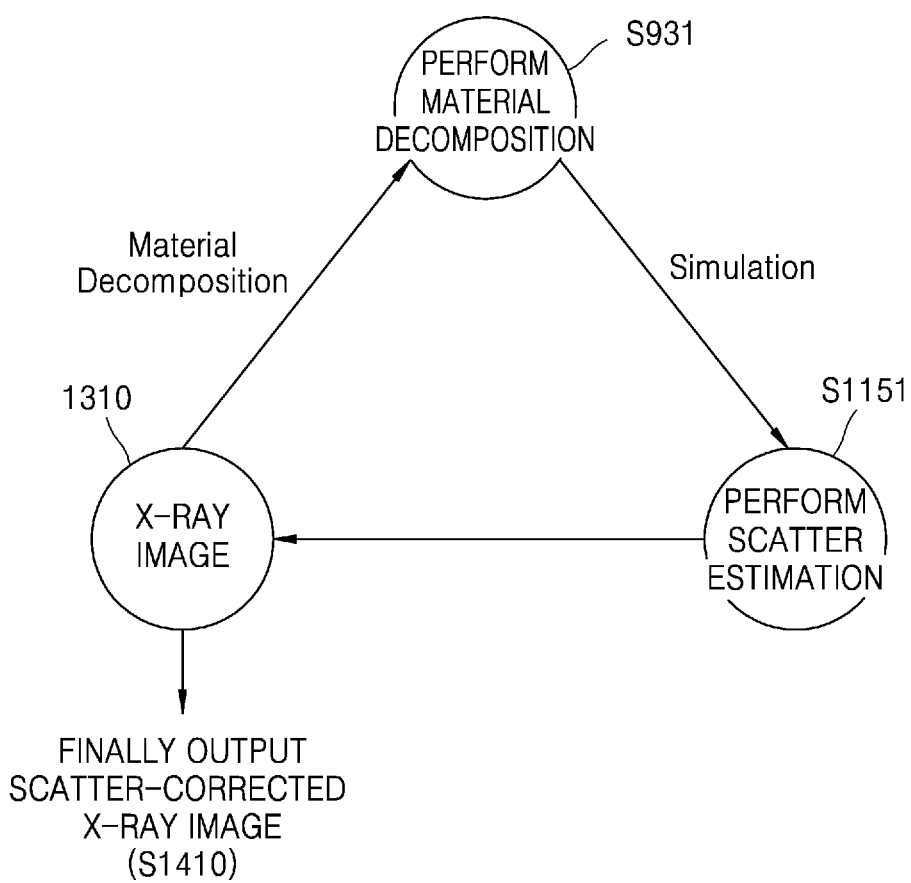
FIG. 14 is a diagram for describing improvement of the quality of an X-ray image through repeated scatter correction according to an embodiment.

FIG. 14 is a diagram for describing improvement of the quality of an X-ray image through repeated scatter correction according to an embodiment. The same elements in FIG. 14 as those of FIGS. 10 through 13 are denoted by the same reference numerals. Hence, the same description of elements of FIG. 14 as that made with reference to FIGS. 10 through 13 will be omitted.

In an embodiment, operation S1151 that is a scatter estimation operation is performed based on first information and second information that are information obtained as a result of operation S931 that is a material decomposition operation, and an X-ray image is scatter corrected based on a scatter map obtained as a result of scatter estimation. When the scatter-corrected X-ray image is within an error range in operation S1360 that is a comparison operation of FIG. 13, the scatter-corrected X-ray image is finally output in operation S1410. When the scatter-corrected X-ray image is not within the error range in operation S1360 of FIG. 13, material decomposition is re-performed based on the scatter-corrected X-ray image. That is, operation S931 that is a material decomposition operation and operation S1151 that is a scatter estimation operation are repeatedly performed based on the scatter-corrected X-ray image 1310.

In an embodiment, a final X-ray image having the best image quality may be generated by repeatedly performing operation S931 and operation S1151 until the scatter-corrected X-ray image is within the error range in operation S1360 of FIG. 13. Accordingly, the first information and the second information are obtained based on the final X-ray image. Accordingly, the accuracy of the first information and the second information may be improved.

An X-ray image processing method according to embodiments may be implemented as program commands executable through various computer means and may be recorded on a computer-readable recording medium. Also, an embodiment may be implemented as a computer-readable recording medium on which one or more programs including instructions for performing an X-ray image processing method are recorded.

The computer-readable recording medium may include program commands, data files, data structures, and the like separately or in combinations. The program commands to be recorded on the computer-readable recording medium may be specially designed and configured for embodiments or may be well-known to and be usable by one of ordinary skill in the art of computer software. Examples of the computer-readable recording medium include a magnetic medium such as a hard disk, a floppy disk, or a magnetic tape, an optical medium such as a compact disk read-only memory (CD-ROM) or a digital versatile disk (DVD), a magneto-optical medium such as a floptical disk, and a hardware device specially configured to store and execute program commands such as a ROM, a RAM, or a flash memory. Examples of the program commands include advanced language codes that may be executed by a computer by using an interpreter or the like as well as machine language codes that are made by a compiler.

An X-ray image processing method according to embodiments may be implemented as a computer program product including a recording medium storing a program for performing: an operation of obtaining a sentence composed of multiple languages; and an operation of obtaining vector values respectively corresponding to words included in the sentence composed of the multiple languages by using a multilingual translation model, converting the obtained vector values into vector values corresponding to a target language, and obtaining a sentence composed of the target language based on the converted vector values.

An X-ray image processing method and an X-ray image processing apparatus using the same according to an embodiment may obtain information about each of a plurality of materials included in an object by using one X-ray image corresponding to a single energy band obtained through one X-ray imaging.

In detail, the X-ray image processing method and the X-ray image processing apparatus using the same according to an embodiment perform only one X-ray imaging in order to obtain information about each of two different materials included in the object. Accordingly, a radiation dose exposed to the object may be minimized when the two different materials are decomposed.

Also, the X-ray image processing method and the X-ray image processing apparatus using the same according to an embodiment may perform scatter correction on an X-ray image based on the information about the two different materials included in the object. Accordingly, the quality of the X-ray image may be improved.

Although the embodiments have been described in detail above, the scope of the disclosure is not limited thereto, and various modifications and improvements made by one of ordinary skill in the art by using the basic concept of the disclosure defined by the claims are also within the scope of the disclosure.

What is claimed is:

1. An X-ray image processing method comprising:
generating a first X-ray image of an object including a plurality of materials comprising a first material and a second material;
obtaining a first partial image and a second partial image based on the first X-ray image, wherein the first partial image represents a first partial area included in the first X-ray image and shows the first material and does not show the second material, and the second partial image represents a second partial area included in the first X-ray image and shows the first material overlapping the second material;
obtaining first information related to a stereoscopic structure of the first material, based on the first partial image included in the first X-ray image; and
obtaining second information about the second material based on the first information and the second partial image,
wherein the first partial area is a different area from the second partial area.

2. The X-ray image processing method of claim 1, wherein the first material is soft tissue, and the second material is a bone.

3. The X-ray image processing method of claim 2, wherein the first information comprises information about a thickness of the soft tissue included in the first partial image.

4. The X-ray image processing method of claim 3, wherein the second information comprises information about a thickness of the bone included in the second partial image, and wherein the second information is obtained based on the information about the thickness of the soft tissue and the second partial image.

5. The X-ray image processing method of claim 2, wherein the second partial image is adjacent to the first partial image in the first X-ray image, and
wherein the second partial image includes a region corresponding to a boundary between the bone and the soft tissue.

6. The X-ray image processing method of claim 1, further comprising outputting a user interface screen comprising at least one of the first information and the second information.

7. The X-ray image processing method of claim 2, further comprising obtaining third information corresponding to a stereoscopic distribution of at least one of the soft tissue or the bone, based on the first information and the second information.

8. The X-ray image processing method of claim 1, further comprising:
performing scatter correction on the first X-ray image based on the first information and the second information, and
updating the first information and the second information based on the scatter-corrected first X-ray image.

9. The X-ray image processing method of claim 1, further comprising generating a scatter map corresponding to a scattered X-ray component in the first X-ray image, based on the first information and the second information.

10. The X-ray image processing method of claim 9, further comprising removing a noise component corresponding to a scattered X-ray in the first X-ray image, based on the scatter map.

11. The X-ray image processing method of claim 9, further comprising:

obtaining a first virtual X-ray image indicating the object, wherein the first virtual X-ray image is generated through projection simulation based on the first information, the second information, and the scatter map; and
determining whether to update the scatter map, based on a result of a comparison between the first virtual X-ray image and the first X-ray image.

12. The X-ray image processing method of claim 1, wherein the first X-ray image is obtained by emitting an X-ray having a single energy band to the object, and
wherein the first partial image and the second partial image correspond to the single energy band.

13. An X-ray image processing apparatus comprising:
a data interface configured to obtain a first X-ray image of an object including a plurality of materials comprising a first material and a second material; and
a controller comprising at least one processor configured to execute at least one instruction to:
obtain a first partial image and a second partial image from the first X-ray image, wherein the first partial image represents a first partial area included in the first X-ray image and shows the first material and does not show the second material, and the second partial image represents a second partial area included in the first X-ray image and shows the first material overlapping the second material,
obtain first information related to a stereoscopic structure of the first material based on the first partial image included in the first X-ray image, and
obtain second information about the second material based on the first information and the second partial image,
wherein the first partial area is a different area from the second partial area.

14. The X-ray image processing apparatus of claim 13, wherein the first material is soft tissue, and the second material is a bone.

15. The X-ray image processing apparatus of claim 14, wherein the first information comprises information about a thickness of the soft tissue included in the first partial image,
wherein the second information comprises information about a thickness of the bone imaged in the second partial image, and
wherein the second information is obtained based on the information about the thickness of the soft tissue and the second partial image.

16. The X-ray image processing apparatus of claim 14, wherein the second partial image is adjacent to the first partial image in the first X-ray image, and
wherein the second partial image includes a region corresponding to a boundary between the bone and the soft tissue.

17. The X-ray image processing apparatus of claim 13, wherein the at least one processor is further configured to:
perform scatter correction on the first X-ray image based on the first information and the second information, and
update the first information and the second information based on the scatter-corrected first X-ray image.

18. The X-ray image processing apparatus of claim 13, wherein the at least one processor is further configured to generate a scatter map corresponding to a scattered X-ray component in the first X-ray image, based on the first information and the second information.

19. The X-ray image processing apparatus of claim 18, wherein the at least one processor is further configured to execute the at least one instruction to:

obtain a first virtual X-ray image indicating the object, wherein the first virtual X-ray image is generated through projection simulation based on the first information, the second information, and the scatter map, and determine whether to update the scatter map, based on a result of a comparison between the first virtual X-ray image and the first X-ray image.

20. A non-transitory computer-readable medium storing instructions which, when executed by at least one processor, cause the at least one processor to perform an X-ray image processing method, the X-ray image processing method comprising:

generate a first X-ray image of an object including a plurality of materials comprising a first material and a second material;

obtaining a first partial image and a second partial image from the first X-ray image, wherein the first partial image represents a first partial area included in the first X-ray image and shows the first material and does not show the second material, and the second partial image represents a second partial area included in the first X-ray image and shows the first material overlapping the second material;

obtaining first information related to a stereoscopic structure of the first material, based on the first partial image included in the first X-ray image; and obtaining second information about the second material based on the first information and the second partial image, wherein the first partial area is a different area from the second partial area.

* * * * *